US006372208B1

(12) United States Patent
Wilson et al.

(10) Patent No.: US 6,372,208 B1
(45) Date of Patent: *Apr. 16, 2002

(54) METHOD OF REDUCING AN IMMUNE RESPONSE TO A RECOMBINANT VIRUS

(75) Inventors: James M. Wilson, Gladwyne; Yiping Yang, Philadelphia; Giorgio Trinchieri, Wynnewood, all of PA (US)

(73) Assignees: The Trustees of the University of Pennsylvania; The Wistar Institute of Anatomy and Biology, both of Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/407,490

(22) Filed: Sep. 28, 1999

Related U.S. Application Data

(63) Continuation of application No. 08/894,488, filed as application No. PCT/US96/03035 on Feb. 23, 1996, now Pat. No. 6,251,957.

(51) Int. Cl.$^7$ .......................... A61K 48/00; C12N 15/86

(52) U.S. Cl. ..................... 424/93.2; 514/44; 435/320.1; 435/325; 435/455; 435/456

(58) Field of Search ................... 514/44; 435/320.1, 435/325, 455, 456; 424/93.21, 93.2

(56) References Cited

U.S. PATENT DOCUMENTS

| 4,658,019 A | 4/1987 | Kung et al. ................. 530/387 |
| 5,017,691 A | 5/1991 | Lee et al. ................... 535/351 |
| 5,166,320 A | 11/1992 | Wu et al. .................... 530/395 |
| 5,240,846 A | 8/1993 | Collins et al. ............ 435/240.1 |
| 5,290,540 A | 3/1994 | Prince et al. ................. 424/45 |
| 5,457,038 A | 10/1995 | Trinchieri et al. ....... 435/69.52 |
| 5,872,154 A | 2/1999 | Wilson et al. .............. 514/885 |

FOREIGN PATENT DOCUMENTS

| EP | 0501233 | 9/1992 |
| EP | 0555880 | 8/1993 |
| EP | 0609739 | 8/1994 |
| NZ | 255 950 | 3/1996 |
| WO | WO 90/05147 | 5/1990 |
| WO | WO 91/18088 | 11/1991 |
| WO | WO 92/19266 | 11/1992 |
| WO | WO 93/00431 | 1/1993 |
| WO | WO 93/06867 | 4/1993 |
| WO | WO 93/19191 | 9/1993 |
| WO | WO 94/04196 | 3/1994 |
| WO | WO 94/12649 | 6/1994 |
| WO | WO 94/17832 | 8/1994 |
| WO | WO 94/28152 | 12/1994 |
| WO | WO 96/12030 | 4/1996 |
| WO | WO 96/12406 | 5/1996 |

OTHER PUBLICATIONS

J. Wilson, "Cystic Fibrosis—Vehicles for Gene Therapy", *Nature*, 365:691–692 Oct. 21, 1993).
J. Wilson et al., "Correction of the Genetic Defect in Hepatocytes from the Watanabe Heritable Hyperlipidemic Rabbit", *Proc. Natl. Acad. Sci. USA*, 85:4421–4425 (Jun. 1988).
J. Wilson et al., "Research Article—Transplantation of Allogeneic Hepatocytes into LDL Receptor Deficient Rabbits Leads to Transient Improvement in Hypercholesterolemia", *Clin. Biol.*, 3:21–26 (Feb. 1991).
J. Wilson et al., "A Novel Mechanism for Achieving Transgene Persistence in vivo after Somatic Gene Transfer into Hepatocytes", *J. Biol. Chem.*, 267(16): 11483–11489 (Jun. 5, 1992).
K. Kozarsky et al., "In Vivo Correction of Low Density Lipoprotein Receptor Deficiency in the Watanabe Heritable Hyperlipidemic Rabbit with Recombinant Adenoviruses", *J. Biol. Chem.*, 269(18):13695–13702 (May 6, 1994).
K. Kozarsky et al., "Adenovirus–Mediated Correction of the Genetic Defect in Hepatocytes from Patients with Familial Hypercholesterolemia", *Somatic Cell and Molecular Genetics*, 19(5):449–458 (Sep. 1993).
K. Kozarsky et al., "Gene Therapy: Adenovirus Vectors", *Curr. Opin. Genet. Devel.*, 3:499–503 (Mar. 1993).
Y. Yang et al., "MHC Class I–Restricted Cytotoxic T Lymphocytes to Viral Antigens Destroy Hepatocytes in Mice Infected with E1–Deleted Recombinant Adenoviruses", *Immunity*, 1:433–442 (Aug. 1994).
Y. Yang et al., "Cellular Immunity to Viral Antigens Limits E1–Deleted Adenoviruses for Gene Therapy", *Proc. Natl. Acad. Sci. USA*, 91:4407–4411 (May 1994).
Y. Yang et al., "Inactivation of E2a in Recombinant Adenoviruses Improves the Prospect for Gene Therapy in Cystic Fibrosis", *Nature Genetics*, 7:362–369 (Jul. 1994).
J. Goldstein et al., "Familial Hypercholesterolemia", in The Metabolic Basis of Inherited Disease, Chapter 448, 6$^{th}$ ed., C.R. Scrivers et al. (eds), McGraw–Hill Information Services Co., New York, pp. 1215–1250 (1989).
J. Goldstein et al., "Defective Lipoprotein Receptors and Atherosclerosis—Lessons from an Animal Counterpart of Familial Hypercholesterolemia", *New Engl. J. Med.*, 309(5):288–296 (Aug. 4, 1983).
J. Goldstein et al., "Disorder of the Biogenesis and Secretion of Lipoproteins", in The Metabolic Basis of Inherited Disease, Chapter 44B, 6$^{th}$ ed., C.R. Scrivers et al., (eds), McGraw–Hill Information Services Co., New York, pp. 1155–1156 (1989).

(List continued on next page.)

*Primary Examiner*—Scott D. Priebe
(74) *Attorney, Agent, or Firm*—Howson and Howson

(57) ABSTRACT

A method of reducing immune response to a viral vector containing a selected transgene is provided. The method involves co-administration of the viral vector and a selected immune modulator capable of inhibiting the formation of neutralizing antibodies and/or CTL elimination of the vectors upon repeated administration.

8 Claims, 7 Drawing Sheets

OTHER PUBLICATIONS

S Ishibashi et al., "Hypercholesterolemia in Low Density Lipoprotein Receptor Knockout Mice and its Reversal by Adenovirus–Mediated Gene Delivery", *J. Clin. Invest., 92:*883–893 (Aug. 1993).

S. Ishibashi et al., "Massive Xanthomatosis and Atherosclerosis in Cholesterol–fed Low Density Lipoprotein Receptor–negative Mice", *J. Clin. Invest., 93:*1885–1893 (May 1994).

M Gafvels et al., "Cloning of a cDNA Encoding a Putative Human Very Low Density Lipoprotein/Apolipoprotein E Receptor and Assignment of the Gene to Chromosome 9pter–p23", *Somatic Cell and Molecular Genetics, 19*(6):557–569 (Sep. 1993).

M Gafvels et al., "Cloning of a Complementary Deoxyribonucleic Acid Encoding the Murine Homolog of the Very Low Density Lipoprotein/Apolipoprotein–E Receptor: Expression Pattern and Assignment of the Gene to Mouse Chromosome 19", *Endocrinology, 135*(1):387–394 (Jul. 1994).

S. Takahashi et al., "Rabbit Very Low Density Lipoprotein Receptor: A Low Density Lipoprotein Receptor–Like Protein with a Distinct Ligand Specificity", *Proc. Natl. Acad. Sci. USA, 89:*9252–9256 (Oct. 1992).

J. Engelhardt et al., "Ablation of E2A in Recombinant Adenoviruses Improves Transgene Persistence and Decreases Inflammatory Response in Mouse Liver", *Proc. Natl. Acad. Sci. USA, 91:*6196–6200 (Jun. 1994).

J. Engelhardt et al., "Adenovirus–Mediated Transfer of the CFTR Gene to Lung of Nonhuman Primates: Biological Efficacy Study", *Human Genet. Ther., 4:*759–769 (Dec. 1993).

J. Engelhardt et al., "Prolonged Transgene Expression in Cotton Rat Lung with Recombinant Adenoviruses Defective in E2a", *Human Gene Ther., 5:*1217–1229 (Oct. 1994).

Y. Watanabe, "Serial Inbreeding of Rabbits with Hereditary Hyperlipidemia (WHHL–Rabbit)", *Atherosclerosis, 36:*261–268 (Jun. 1980).

K. Tanzawa et al., "WHHL–Rabbit: A Low Density Lipoprotein Receptor–Deficient Animal Model for Familial Hypercholesterolemia", *FEBS Letters, 118*(1):81–84 (Aug. 1980).

M. Horwitz, "Adenoviridae and Their Replication", *Virology,* 2$^{nd}$ ed., ed. B.B. Fields, Raven Press, Ltd., New York, Chapter 60, pp. 1679–1721 (1990).

M. Grossman et al., "Towards Liver–Directed Gene Therapy: Retrovirus–Mediated Gene Transfer into Human Hepatocytes", *Som. Cell. and Mol. Gen., 17*(6):601–607 (Nov. 1991).

M. Boshart et al., "A Very Strong Enhancer is Located Upstream of an Immediate Early Gene of Human Cytomegalovirus", *Cell, 41:*521–530 (Jun. 1985).

C. Wu et al., "Targeting Genes: Delivery and Persistent Expression of a Foreign Gene Driven by Mammalian Regulatory Elements in Vivo", *J. Biol. Chem., 264*(29):16985–16987 (Oct. 15, 1989).

K. Fisher et al., "Biochemical and Functional Analysis of an Adenovirus–Based Ligand Complex for Gene Transfer", *Biochem. J., 299:*49–58 (Apr. 1, 1994).

C. Lauglin et al., "Cloning of Infectious Adeno–associated Virus Genomes in Bacterial Plasmids", *Gene, 23:*65–73 (Jul. 1983).

J. Price et al., "Lineage Analysis in the Vertebrate Nervous System by Retrovirus–mediated Gene Transfer", *Proc. Natl. Acad. Sci. USA, 84:*156–160 (Jan. 1987).

T. Kost et al., "The Nucleotide Sequence of the Chick Cytoplasmid beta–actin Gene", *Nucl. Acids. Res., 11*(23):8287–8301 (Dec. 11, 1983).

J. Schreiber et al., "Recombinant Retroviruses Containing Novel Reporter Genes", *BioTechniques, 14*(5):818–823 (May 1993).

J. Riordan et al., "Identification of the Cytstic Fibrosis Gene: Cloning and Characterization of the Complementary DNA", *Science, 245:*1066–1073 (Sep. 8, 1989).

M. Brown et al., "A Receptor–Mediated Pathway for Cholesterol Homeostasis", *Science, 232:*34–47 (Apr. 4, 1986).

T. Yamamoto et al., "The Human LDL Receptor: A Cysteine–Rich Protein with Multiple Alu Sequences in its mRNA", *Cell, 39:*27–38 (Nov. 1984).

R. Samulski et al., "Helper–Free Stocks of Recombinant Adeno–Associated Viruses: Normal Integration Does Not Require Viral Gene Expression", *J. Virol., 63*(9):3822–3828 (Sep. 1989).

T. Shenk et al., "Genetic Analysis of Adenoviruses", *Curr. Topics in Microbiol. and Immunol., 111:*1–39 (1984).

P. Hearing et al., "Identification of a Repeated Sequence Element Required for Efficient Encapisidation of the Adenovirus Type 5 Chromosome", *J. Viol., 61*(8):2555–2558 (Aug. 1987).

M. Grable et al., "Adenovirus Type 5 Packaging domain is composed of a Repeated Element that is Functionally Redundant", *J. Viol., 64*(5):2047–2056 (May 1990).

M. Grable et al., "Cis and Trans Requirements for the Selective Packaging of Adenovirus Type 5 DNA", *J. Viol., 66*(2):723–731 (Feb. 1992).

F. Wittmaack et al., "Localization and Regulation of the Human Very Low Density Lipoprotein/Apolipoprotein–E Receptor: Trophoblast Expression Predicts a Role for the Receptor in Placental Lipid Transport", *Endocrinol., 136*(1):340–348 (Jan. 1995).

M. Rosenfeld et al., "In Vivo Transfer of the Human Cystic Fibrosis Transmembrane Conductance Regulator Gene to the Airway Epithelium", *Cell, 68:*143–155 (Jan. 10, 1992).

J. Logan et al., "Adenovirus Tripartite Leader Sequence Enhances Translation of mRNAs Late After Infection", *Proc. Natl. Acad. Sci. USA, 81:*3655–3659 (Jun. 1984).

P. Van Der Vliet et al., "Thermolabilie DNA Binding Proteins from Cells Infected with a Temperature–Sensitive Mutant of Adenovirus Defective in Viral DNA Synthesis", *J. Virol., 15*(2):348–354 (Feb. 1975).

P. Scott, "IL–12: Initiation Cytokine for Cell–Mediated Immunity", *Science,* 260:496–497 (Apr. 1993).

R. Manetti et al., "Natural Killer Cell Stimulatory Factor (Interleukin 12 [IL–12]) Induces T Helper Type 1 (Th1)—Specific Immune Responses and Inhibits the Development of IL–4–Producing Th Cells", *J. Exp. Med., 177:*1199–1204 (Apr. 1993).

A. D'Andrea et al., "Production of Natural Killer Cell Stimulatory Factor (Interleukin–12) by Peripheral Blood Mononuclear Cells", *J. Exp. Med., 176:*1387–1398 (Nov. 1992).

S. Morris et al., "Effects of IL–12 on in Vivo Cytokine Gene Expression and Ig Isotype Selection", *J. Immunol., 152:*1047–1056 (Feb. 1994).

F. Heinzel et al., "Recombinant Interleukin 12 Cures Mice Infected with Leishmania Major", *J. Exp. Med.*, 177:1505–1509 (May 1993).

T. Yokota et al., "Isolation and Characterization of a Human Interleukin cDNA Clone, Homologous to Mouse B–Cell Stimulatory Factor 1, that Expresses B–cell– and T–cell––Stimulating Activities", *Proc. Natl. Acad. Sci. USA*, 83:5894–5898 (Aug. 1986).

F. Durie et al., "The Role of CD40 in the Regulation of Humoral and Cell–Mediated Immunity", *Immunol. Today*, 15(9):406–410 (Sep. 1994).

J. Cohen, "Naked DNA Points Way to Vaccines", *Science*, 259:1691–1692 (Mar. 19, 1993).

A. McKnight et al., "Effects of IL–12 on Helper T Cell–Dependent Immune Responses in Vivo", *J. Immunol.*, 152:2172–2179 (Mar. 1994).

L. Alfonso et al., "The Adjuvant Effect of Interleukin–12 in a Vaccine Against Leishmania Major", *Science*, 263:235–237 (Jan. 1994).

J. Sypek et al., "Resolution of Cutaneous Leishmaniasis: Interleukin–12 Initiates a Protective T Helper Type 1 immune Response", *J. Exp. Med.*, 177:1797–1802 (Jun. 1993).

C–S. Hsieh et al., "Development of Th1 CD4+ Cells Through IL–12 Produced by Listeria–Induced Macrophages", *Science*, 260:547–549 (Apr. 1991).

S. Chan et al., "Induction of Interferon Gamma Production by Natural Killer Cell Stimulatory Factor: Characterization of the Responder Cells and Synergy with Other Inducers", *J. Exp. Med.*, 173:869–879 (Apr. 1991).

Y. Yang et al., "Transient Immune Blockade Prevents Formation of a Neutralizing Antibody to Recombinant Adenovirus and Allow Repeated Gene Transfer to Mouse Liver", *Gene Therapy*, 3(5):412–420 (Mar. 1996).

Y. Yang et al., "Recombinant IL–12 Prevents Formation of Blocking IgA Antibodies to Recombinant Adenovirus and Allows Repeated Gene Therapy to Mouse Lung", *Nature Medicine*, 1(9):890–893 (Sep. 1995).

M. Lee et al., "The Constitutive Expression of the Immunomodulatory gp19k Protein in E1–, E3– Adenoviral Vectors Strongly Reduces the Host Cytotoxic T Cell Response Against the Vector", *Gene Therapy*, 2:256–262 (Jun. 1995).

B. Fang et al., "Gene Therapy for Hemophilia B: Host Immno–Suppression Prolongs the Therapeutic Effect of Adenovirus–Mediated Factor IX Expression", *Human Gene Therapy*, 6:1039–1044 (Aug. 1995).

J. Zabner et al., "Safety and Efficacy of Repetitive Adenovirus–Mediated Transfer of CFTR cDNA to Airway Epithelia of Primates and Cotton Rats", *Nature Genetics*, 6:75–83 (Jan. 1994).

A. Elshami et al., "The Role of Immunosuppression in the Efficacy of Cancer Gene Therapy Using Adenovirus Transfer of the Herpes Complex Thymidine Kinase Gene", *Annals of Surgery*, 222(3):298–310 (Sep. 1995).

J. Wilson, "Gene Therapy for Cystic Fibrosis: Challenges and Future Directions", *J. Clin. Invest.*, 96:2547–2554 (Dec. 1995).

E. Marshall, "Gene Therapy's Growing Pains", *Science*, 269:1050–1055 (Aug. 1995).

Y. Dai et al., "Cellular and Humoral Immune Response to Adenoviral Vectors Containing Factor IX Gene: Tolerization of Factor IX and Vector Antigens Allows for Long–Term Expression", *Proc. Natl. Acad. Sci. USA*, 92:14401–1405 (Feb. 1995).

J. Engelhardt et al., "Direct Gene Transfer of Human CFTR into Human Bronchial Epithelia of Xeongrafts with E1–Deleted Adenoviruses",*Nature Genetics, 4:*27–34 (May 1993).

H. Tahara et al., "Antitumor Effects of Interleukin–12 (IL–12): Applications for the Immunotherapy and Gene Therapy of Cancer", *Gene Therapy*, 2:96–106 (Mar. 1995).

A. Coghlan, "Gene Dream Fades Away", *Focus*, 145:14–15 (Nov. 25, 1995).

Brown, "Gene Therapy 'Oversold' by Researchers, Journalists", The Washington Post (Dec. 9, 1995).

R. Mulligan, "The Basic Science of gene Therapy", *Science*, 260:926–930 (May 14, 1993).

E. Kremer et al., "Adenovirus and Adeno–associated Virus Mediated Gene Transfer", *British Medical Bulletin*, 51:31–44 (Jan. 1995).

S. Orkin et al., "Report and Recommendation of the Panel to Assess the NIH Investment in Research on Gene Therapy" *The Washington Post* (Dec. 7, 1995).

K. Harada et al., "Growth Inhibition of Subcutaneously Trans–planted Human Glioma by Transfection–Induced Tumor Necrosis Factor–α and Augmentation of the Effect by γ–Interferon", *J. Neuro–Onc.*, 22:221–225 (1994).

D. Losordo et al., "Use of the Rabbit Ear Artery To Serially Assess Foreign Protein Secretion After Site–Specific Arterial Gene Transfer in Vivo", *Circulation*, 89(2):785–792 (Feb. 1994).

E. Raz et al., "Systemic Immunological Effects of Cytokine Genes Injected into Skeletal Muscle",*Proc. Natl. Acad. Sci. USA*, 90:4523–4527 (May 1993).

M. Kay et al., "In vivo Hepatic Gene Therapy: Complete Albeit Transient Correction of Factor IX Deficiency in Hemophilia B Dogs", *Proc. Natl. Acad. Sci. USA*, 91:2353–2357 (Mar. 1994).

B. Quantin et al., "Adenovirus as an Expression Vector in Muscle Cells in vivo", *Proc. Natl. Acad. Sci. USA*, 89:2581–2584 (Apr. 1992).

R. Simon et al., "Adenovirus–Mediated Transfer of the CFTR Gene to Lung of Nonhuman Primates: Toxicity Study", *Hum. Gene. Ther.*, 4:771–780 (Feb. 1993).

Stratford–Perricaudet et al., "Evaluation of the Transfer and Expression in Mice of an Enzyme Encoding Gene Using a human Adenovirus Vector", *Hum. Gene. Ther.*, 1:241–256 (May 1990).

Y. Yang et al., "Cellular and Humoral Immune Response to Viral Antigens Create Barriers to Lung–Directed Gene Therapy with Recombinant Adenoviruses", *J. Viol.*, 69(4):2004–2015 (Apr. 1995).

J. Zabner et al., "Adenovirus–Mediated Gene Transfer Transiently Corrects the Chloride Transport Defect in Nasal Epithelia of Patients with Cystic Fibrosis",*Cell, 75:*207–216 (Oct. 1993).

R. Crystal et al., "Administration of an Adenovirus Containing the Human CFTR cDNA to the Respiratory Tract of Individuals with Cystic Fibrosis", *Nat. Genet.*, 8:42–51 (Sep. 1994).

Z. Zsengeller et al., "Persistence of Replication–Deficient Adenovirus–Mediated Gene Transfer in Lungs of Immune–Deficient (nu/nu) Mice", *Hum. Gene. Ther.*, 6:457–467 (Apr. 1995).

T. Smith et al., "Adenovirus Mediated Expression of Therapeutic Plasma Levels of Human Factor IX in Mice", *Nat. Genet.*, 5:397 (Dec. 1993).

S. Yei et al., "Adenovirus–Mediated Gene Transfer for Cystic Fibrosis: Quantitative Evaluation of Repeated in Vivo Vector Administration to the Lung", *Gene Therapy*, *1*:192–200 (Jun. 1994).

B. Trapnell et al., "Pharmacologic Immunomodulation Enhances Repeated in Vivo Adenovirus–Mediated Gene Transfer", *J. Cell Biochem., 21A*:415, Abstract No. C6–449 (Apr. 1995).

Jooss et al., "Cyclophosphamide Diminishes Inflammation and Prolongs Transgene Expression Following Delivery of Adenoviral Vectors to Mouse Liver and Lung", *Hum. Gene. Ther., 7*:1555–1566 (Aug. 20, 1996).

Duboc et al., "Interest of Immunosuppression for Maintaining Transgene Expression after Direct Injection in Myocardium of a Recombinant Adenovirus", *Circulation: Abstracts from the 67$^{th}$ Scientific Sessions,* vol. 90, No. 4, Part 2, Abstract # 2784 (Oct. 1994).

"The Immune System: An Introduction", Fundamental Immunology, 3$^{rd}$ edition, Raven Press Ltd., New York, p. 13 (1993).

T. S. Ranheim, "Characterization of Mutants Within the Gene for the Adenovirus E3 14.7 Kilodalton Protein Which Prevents Cytolysis By Tumor Necrosis Factor", *J. Virol., 67*(4):2159–2167 (Apr. 1993).

METHOD OF REDUCING AN IMMUNE RESPONSE TO A RECOMBINANT VIRUS

CROSS-REFERENCE TO RELATED APPLICATIONS

This is a continuation of U.S. patent application Ser. No. 08/894,488, filed Aug. 22, 1997, now U.S. Pat. No. 6,251,957, which is a 35 USC §371 of PCT/US96/03035, filed Feb. 23, 1996, which claims the benefit of the priority of U.S. patent application Ser. No. 08/585,397, filed Jan. 11, 1996, now abandoned, and U.S. patent application Ser. No. 08/394,032, filed Feb. 24, 1995, now U.S. Pat. No. 5,872,154.

This invention was supported by the National Institutes of Health Grant Nos. DK 47757-02 and AI 34412-02. The United States government has certain rights in this invention.

FIELD OF THE INVENTION

The present invention relates generally to gene therapy, and more specifically, to methods of administering viral vectors used in gene therapy.

BACKGROUND OF THE INVENTION

Recombinant adenoviruses have emerged as attractive vehicles for in vivo gene transfer to a wide variety of cell types. The first generation vectors, which are rendered replication defective by deletion of the immediate early genes E1a and E1b, are capable of highly efficient in vivo gene transfer into nondividing target cells [M. Kay et al, *Proc. Natl. Acad. Sci. USA*, 91:2353–2357 (1994); S. Ishibashi et al, *J. Clin. Invest.*, 92:883–893 (1993); B. Quantin et al, *Proc. Natl. Acad. Sci. USA*, 89:2581–2584 (1992); M. Rosenfeld et al, *Cell*, 68:143 (1992); R. Simon et al, *Hum. Gene Thera.*, 4:771 (1993); Rosenfeld et al, *Science*, 252:431–434 (1991); Stratford-Perricaudet et al, *Hum. Gene Ther.*, 1:241–256 (1990)].

Immune responses of the recipient to the viral vector, the transgene carried by the vector, and the virus-infected cells have emerged as recurring problems in the initial application of this technology to animals and humans [Yang et al, *J. Virol.*, 69:2004–2015 (1995) (Yang I)]. In virtually all models, including lung-directed and liver-directed gene therapy, expression of the transgene is transient and associated with the development of pathology at the site of gene transfer.

The transient nature of transgene expression from recombinant adenoviruses is due, in part, to the development of antigen specific cellular immune responses to the virus-infected cells and their subsequent elimination by the host. Specifically, first generation vectors, although deleted in the E1a region of the vector, express viral proteins in addition to the transgene. These viral proteins activate cytotoxic T lymphocytes (CTL) [Y. Dai et al, *Proc. Natl. Acad. Sci. USA*, 92: 1401–1405 (1995); Y. Yang et al. *Proc. Natl. Acad. Sci. USA*, 91:4407–4411 (1994) (Yang II); and Y. Yang et al, *Immunity*, 1:433–442 (1994) (Yang III)]. The collaboration of CTLs directed against newly synthesized viral proteins and viral specific T helper cells [Zabner et al, *Cell*, 75:207–216 (1993); Crystal et al, *Nat. Genet.*, 8:42–51 (1994)] leads to the destruction of the virus-infected cells.

Another antigenic target for immune mediated clearance of virally-infected cells can be the product of the transgene when that transgene expresses a protein that is foreign to the treated host. CTLs are thus an important effector in the destruction of target cells, with activation occurring in some cases in the context of the transgene product, or of the viral-synthesized proteins, both of which are presented by MHC class I molecules [Yang I; and Zsengeller et al, *Hum. Gene Thera.*, 6:457–467 (1995)]. These immune responses have also been noted to cause the occurrence of associated hepatitis that develops in recipients of in vivo liver directed gene therapy within 2–3 weeks of initial treatment.

Another limitation of recombinant adenoviruses for gene therapy has been the difficulty in obtaining detectable gene transfer upon a second administration of virus. This limitation is particularly problematic in the treatment of single gene inherited disorders or chronic diseases, such as cystic fibrosis (CF), that will require repeated therapies to obtain life-long genetic reconstitution. Diminished gene transfer following a second therapy has been demonstrated in a wide variety of animal models following intravenous or intratracheal delivery of virus [T. Smith et al, *Gene Thera.*, 5:397 (1993); S. Yei et al, *Gene Thera.*, 1:192–200 (1994); K. Kozarsky et al, *J. Biol. Chem.*, 269:13695 (1994)]. In each case, resistance to repeated gene therapy was associated with the development of neutralizing anti-adenovirus antibody, which thwarted successful gene transfer following a second administration of virus.

Potential solutions for these problems have been directed towards the development of second generation recombinant viruses [Y. Yang et al, *Nat. Genet.*, 7:362–369 (1994) (Yang IV); and J. Engelhardt et al, *Hum. Gene Thera.*, 5:1217 (1994)] designed to diminish the expression of newly synthesized viral proteins, and the use of non-immunogenic transgenes, to prevent CTL activation.

Thus, there remains a need in the art for a method and composition for improving the efficiency of gene transfer during repeated administrations of viral gene therapy.

SUMMARY OF THE INVENTION

The present invention provides a method of gene therapy and compositions for use therein which result in a reduced immune response to the recombinant viral vector used to accomplish the therapy. The method involves co-administering with the gene therapy viral vector a selected immune modulator, which substantially reduces the occurrence of neutralizing antibody responses directed against the vector encoded antigens and/or cytolytic T cell elimination of the viral protein containing cells. This method is particularly useful where readministration of the recombinant virus is desired. According to this method the immune modulator may be administered prior to or concurrently with the recombinant viral vector bearing the transgene to be delivered.

Other aspects and advantages of the present invention are described further in the following detailed description of the preferred embodiments thereof.

DETAILED DESCRIPTION OF THE INVENTION

Figure 1A:
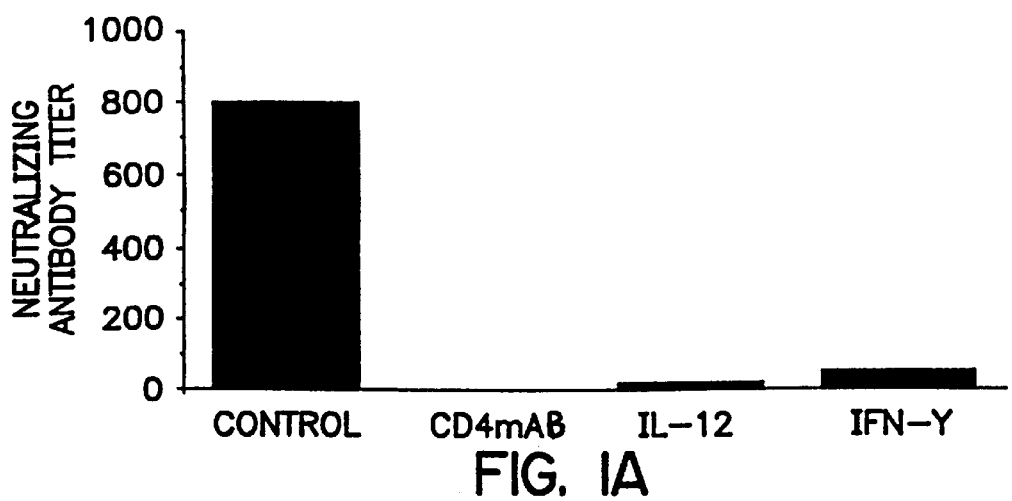
FIG. 1A is a graph summarizing neutralizing antibody titer present in brochoalveolar lavage fluid (BAL) samples of C57BL-6 mice adenovirus-infected on day 0 and necropsied on day 28 as described in Example 2. Control represents normal mice ("control"); CD4 mAB represents CD4$^+$ cell-depleted mice; IL-12 represents mice treated with IL-12 on days 0 and +1 and IFN-γ represent mice treated with IFN-γ on days 0 and +1. Data are presented as the mean±1 standard deviation for three independent experiments.

The present invention provides methods and compositions for improving an animal or human's ability to tolerate administration of gene therapy viral vectors. The invention provides methods to transiently prevent activation of CD4$^+$ T cells which are involved in both cellular and humoral immune barriers to gene therapy. The methods involve administering to an individual receiving a gene therapy vector a suitable amount of a preferably short-acting immune modulator. The immune modulator is preferably administered concurrently with administration of the gene therapy vector, i.e., a recombinant virus, used to deliver a therapeutic transgene desired for gene therapy. The immune modulator may also be administered before or after administration of the vector.

The method of this invention, which prevents the development of adverse cellular and humoral immune responses to gene therapy viral vectors, is based on immune suppression to block activation of T helper cells, specifically CD4 function, and B cells. In contrast to the prior art, which involved chronic immune suppression by continuous administration of non-specific immune suppressing drugs; the present invention uses a transient approach to immunosuppression. Without wishing to be bound by theory, the inventors theorize that the primary stimulus for immune activation is viral capsid proteins from the recombinant vector. Chronic immune suppression is not necessary in such a scenario. Specifically, transient ablation of CD4 function at or near the time of recombinant virus administration according to this invention prevents the formation of neutralizing antibody, thereby allowing efficient gene transfer following at least two subsequent administrations of gene therapy viral vectors.

As illustrated below, administration of immune modulators according to the method of this invention is preferably conducted only at the time of virus administration. However, more prolonged immune modulation than is necessary in the following examples of gene transfer to mouse liver and/or lung may be needed, depending upon the manner in which the antigens are presented in different gene therapy protocols. Thus, the method of transient immune modulation of the invention may, in certain circumstances, be combined with long term immuno-suppression or other immunomodulatory therapies.

I. Immune Modulators

The selected immune modulator is defined herein as an agent capable of inhibiting the formation by activated B cells of neutralizing antibodies directed against the recombinant viral vector and/or capable of inhibiting cytolytic T lymphocyte (CTL) elimination of the vector. The immune modulator may be selected to interfere with the interactions between the T helper subsets ($T_{H1}$ or $T_{H2}$) and B cells to inhibit neutralizing antibody formation. Alternatively, the immune modulator may be selected to inhibit the interaction between $T_{H1}$ cells and CTLs to reduce the occurrence of CTL elimination of the vector. More specifically, the immune modulator desirably interferes with or blocks. the function of the CD4 T cells.

Immune modulators for use in inhibiting neutralizing antibody formation according to this invention may be selected based on the determination of the immunoglobulin subtype of any neutralizing antibody produced in response to the viral vector. The neutralizing antibody that develops in response to administration of a gene therapy viral vector is frequently based on the identity of the virus, the identity of the transgene, what vehicle is being used to deliver the vector and/or the target location or tissue type for viral vector delivery.

For example, $T_{H2}$ cells are generally responsible for interfering with the efficient transfer of genes administered during gene therapy. This is particularly true when the viral vector is adenovirus-based. More particularly, the inventors have determined that neutralizing antibodies of the subtypes, $IgG_1$ and IgA, which are dependent upon the interaction between $T_{H2}$ cells and B cells, appear to be the primary cause of major neutralizing antibodies against adenoviral vectors.

The identity of the neutralizing antibody induced by administering a specific gene therapy recombinant viral vector is readily determined in animal trials. See, e.g., Example 6. For example, administration of adenoviral vectors via the lungs generally induces production of IgA neutralizing antibody, while administration of adenoviral vectors via the blood generally induces $IgG_1$ neutralizing antibody. In these cases, a $T_{H2}$-dependent immune response interferes with transfer of the adenovirus-based viral vector carrying a therapeutic transgene.

Where the neutralizing antibody induced by viral vector administration is a $T_{H2}$ mediated antibody, such as IgA or $IgG_1$, the immune modulator selected for use in this method desirably suppresses or prevents the interaction of $T_{H2}$ cells with B cells. Alternatively, if the induced neutralizing antibody is found to be a $T_{H1}$ mediated antibody, such as $IgG_{2A}$, the immune modulator desirably suppresses or prevents the interaction of $T_{H1}$ cells with B cells. Where the reduction of CTL elimination of the viral vectors is desired as well as the blocking of neutralizing antibody formation, the immune modulator is selected for its ability to suppress or block $CD4^+$ $T_{H1}$ cells to permit prolonged residence of the viral vector in vitro.

The immune modulators may comprise soluble or naturally occurring proteins, including cytokines and monoclonal antibodies. The immune modulators may comprise other pharmaceuticals. In addition, the immune modulators according to the invention may be used alone or in combination with one another. For example, cyclophosphamide and the more specific immune modulator anti-CD4 monoclonal antibody may be co-administered. In such a case, cyclophosphamide serves as an agent to block $T_{H1}$ activation and to stabilize transgene expression beyond the period of transient immune blockade induced by anti-CD4 MAb treatment.

A suitable amount or dosage of the selected immune modulator will depend primarily on the identity of the modulator, the amount of the recombinant vector bearing the transgene that is initially administered to the patient, and the method and/or site of delivery of the vector. These factors can be evaluated empirically by one of skill in the art using the procedures described herein. Other secondary factors such as the condition being treated, the age, weight, general health, and immune status of the patient, may also be considered by a physician in determining the dosage of immune modulator to be delivered to the patient in conjunction with a gene therapy vector according to this invention.

Generally, for example, a therapeutically effective human dosage of a protein immune modulator, e.g., IL-12 or IFN-γ, is administered in the range of from about 0.5 µg to about 5 mg per about $1 \times 10^7$ pfu/ml virus vector. Various dosages may be determined by one of skill in the art to balance the therapeutic benefit against any adverse side effects.

A. Monoclonal Antibodies and Soluble Proteins

Preferably, the method of inhibiting an adverse immune response to the gene therapy vector involves non-specific inactivation of $CD4^+$ cells. One such method comprises administering an appropriate monoclonal antibody. Preferably, such blocking antibodies are "humanized" to prevent the recipient from mounting an immune response to the blocking antibody. A "humanized antibody" refers to an antibody having its complementarily determining regions (CDRS) and/or other portions of its light and/or heavy variable domain framework regions derived from a non-human donor immunoglobulin, the remaining immunoglobulin-derived parts of the molecule being derived from one or more human immunoglobulins. Such antibodies can also include antibodies characterized by a humanized heavy chain associated with a donor or acceptor unmodified light chain or a chimeric light chain, or vice versa. Such "humanization" may be accomplished by methods known to the art. See, for example, G. E. Mark and E. A. Padlan, *"Chap. 4. Humanization of Monoclonal Antibodies"*, The Handbook of Experimental Pharmacology, vol. 113, Springer-Verlag, New York (1994), pp. 105–133, which is incorporated by reference herein.

Other suitable antibodies include those that specifically inhibit or deplete $CD4^+$ cells, such as an antibody directed against cell surface CD4. Depletion of $CD4^+$ cells has been shown by the inventors to inhibit the CTL elimination of the viral vector. Such modulatory agents include but are not limited to anti-T cell antibodies, such as anti-OKT3+ [see, e.g., U.S. Pat. No. 4,658,019; European Patent Application No. 501,233, published Sep. 2, 1992]. See Example 2 below, which employs the commercially available antibody GK1.5 (ATCC Accession No. TIB207) to deplete $CD4^+$ cells.

Alternatively, any agent that interferes with or blocks the interactions necessary for the activation of B cells by $T_H$ cells, and thus the production of neutralizing antibodies, is useful as an immune modulator according to the methods of this invention. For example, B cell activation by T cells requires certain interactions to occur [F. H. Durie et al, *Immunol. Today*, 15(9):406–410 (1994)], such as the binding of CD40 ligand on the T helper cell to the CD40 antigen on the B cell, and the binding of the CD28 and/or CTLA4 ligands on the T cell to the B7 antigen on the B cell. Without both interactions, the B cell cannot be activated to induce production of the neutralizing antibody.

The CD40 ligand (CD40L)-CD40 interaction is a desirable point to block the immune response to gene therapy vectors because of its broad activity in both T helper cell activation and function as well as the absence of redundancy in its signaling pathway. A currently preferred method of the present invention thus involves transiently blocking the interaction of CD40L with CD40 at the time of adenoviral vector administration. This can be accomplished by treating with an agent which blocks the CD40 ligand on the $T_H$ cell and interferes with the normal binding of CD40 ligand on the T helper cell with the CD40 antigen on the B cell. Blocking CD40L-CD40 interaction prevents the activation of the T helper cells that contributes to problems with transgene stability and readministration.

Thus, an antibody to CD40 ligand (anti-CD40L) [available from Bristol-Myers Squibb Co; see, e.g., European patent application 555,880, published Aug. 18, 1993] or a soluble CD40 molecule can be a selected immune modulator in the method of this invention.

Alternatively, an agent which blocks the CD28 and/or CTLA4 ligands present on T helper cells interferes with the normal binding of those ligands with the antigen B7 on the B cell. Thus, a soluble form of B7 or an antibody to CD28 or CTLA4, e.g., CTLA4-Ig [available from Bristol-Myers Squibb Co;.see, e.g., European patent application 606,217, published Jul. 20, 1994] can be the selected immune modulator in the method of this invention. This method has greater advantages than the below-described cytokine administration to prevent $T_{H2}$ activation,, because it addresses both cellular and humoral immune responses to foreign antigens.

B. Cytokines

Still other immune modulators which inhibit the $T_H$ cell function may be employed in the methods of this invention.

Thus, in one embodiment, an immune modulator for use in this method which selectively inhibits the function of the $T_{H1}$ subset of CD4+ T helper cells may be administered at the time of primary administration of the viral vector. One such immune modulator is interleukin-4 (IL-4). IL-4 enhances antigen specific activity of $T_{H2}$ cells at the expense of the $T_{H1}$ cell function [see, e.g., Yokota et al, *Proc. Natl. Acad. Sci., USA*, 83:5894–5898 (1986); U.S. Pat. No. 5,017, 691]. It is envisioned that other immune modulators that can inhibit $T_{H1}$ cell function will also be useful in the methods of this invention.

In another embodiment, the immune modulator can be a cytokine that prevents the activation of the $T_{H2}$ subset of T helper cells. The success of this method depends on the relative contribution that $T_{H2}$ dependent Ig isotypes play in virus neutralization, the profile of which may be affected by strain, the species of animal as well as the mode of virus delivery and target organ.

A desirable immune modulator for use in this method which selectively inhibits the CD4+ T cell subset $T_{H2}$ function at the time of primary administration of the viral vector includes interleukin-12 (IL-12). IL-12 enhances antigen specific activity of $T_{H1}$ cells at the expense of $T_{H2}$ cell function [see, e.g., European Patent Application No. 441, 900; P. Scott, *Science*, 260:496–497 (1993); R. Manetti et al, *J. Exp. Med.*, 177:1199 (1993); A. D'Andrea et al, *J. Exp. Med.*, 176:1387 (1992)]. IL-12 for use in this method is preferably in protein form. Human IL-12 may be recombinantly produced using known techniques or may be obtained commercially. Alternatively, it may be engineered into a viral vector (which optionally may be the same as that used to express the transgene) and expressed in a target cell in vivo or ex vivo.

$T_{H2}$ specific ablation with IL-12 is particularly effective in lung-directed gene therapies where IgA is the primary source of neutralizing antibody. In liver-directed gene therapy, both $T_{H1}$ and $T_{H2}$ cells contribute to the production of virus specific antibodies. However, the total amount of neutralizing antibody can be diminished with IL-12.

Another selected immune modulator which performs a similar function is gamma interferon (IFN-γ) [S. C. Morris et al, *J. Immunol.*, 152:1047–1056 (1994); F. P. Heinzel et al, *J. Exp. Med.*, 177:1505 (1993)]. IFN-γ is believed to mediate many of the biological effects of IL-12 via secretion of activated macrophages and T helper cells. IFN-γ also partially inhibits IL-4 stimulated activation of $T_{H2}$. IFN-γ may also be obtained from a variety of commercial sources.

Alternatively, it may be engineered into a viral vector and expressed in a target cell in vivo or ex vivo using known genetic engineering techniques.

Preferably, such cytokine immune modulators are in the form of human recombinant proteins. These proteins may be produced by methods extant in the art. Active peptides, fragments, subunits or analogs of the known immune modulators described herein, such as IL-12 or gamma interferon, which share the $T_{H2}$ inhibitory function of these proteins, will also be useful in this method when the neutralizing antibodies are $T_{H2}$ mediated.

As illustrated in the examples below, the cytokines IL-12 (which activates $T_{H1}$ cells to secrete IFN-γ) and IFN-γ are shown to ablate humoral immunity only (i.e., they inhibit $T_{H2}$ differentiation). Co-administration of either cytokine at the time of virus instillation prevented formation of IgA and allowed efficient re-administration of virus.

To permit an effective second administration of virus in liver-directed gene therapy, the method may preferably comprise administration of more than one cytokine, specific dosing regimens and/or co-administration of an additional immune modulator, such as one or more of the antibodies discussed above. The use of cytokines is advantageous because cytokines are natural products, and thus not likely to generate any adverse immune responses in the patient to which they are administered.

C. Other Pharacauticals

Other immune modulators or agents that non-specifically inhibit immune function, i.e., cyclosporin A or cyclophosphamide, may also be used in the methods of the invention. For example, a short course of cyclophosphamide has been demonstrated to successfully interrupt both CD4 and CD8 T helper cell activation to adenovirus capsid protein at the time of virus delivery to the liver. As a result, transgene expression was prolonged and, at higher doses, formation of neutralizing antibody was prevented, allowing successful vector readministration. In the lung, cyclophosphamide prevented formation of neutralizing antibodies at all doses and stabilized transgene expression at high dose.

II. Viral Vectors

Suitable viral vectorsuseful in gene therapy are well known, including retroviruses, vaccinia viruses, poxviruses, adenoviruses and adeno-associated viruses, among others. The method of this invention is anticipated to be useful with any virus which forms the basis of a gene therapy vector. However, exemplary viral vectors for use in the methods of the invention are adenovirus vectors [see, e.g., M. S. Horwitz et al, "Adenoviridae and Their Replication", *Virology,* second edition, pp. 1712, ed. B. N. Fields et al, Raven Press Ltd., New York (1990); M. Rosenfeld et al, *Cell,* 68:143–155 (1992); J. F. Engelhardt et al, *Human Genet. Ther.,* 4:759–769 (1993); Yang IV; J. Wilson, *Nature,* 365:691–692 (October 1993); B. J. Carter, in "Handbook of Parvoviruses", ed. P. Tijsser, CRC Press, pp. 155–168 (1990).

Particularly desirable are human type C adenoviruses (Ad), including serotypes Ad2 and Ad5, which have been rendered replication defective for gene therapy by deleting the early gene locus that encodes E1a and E1b. There has been much published on the use of E1 deleted adenoviruses in gene therapy. See, K. F. Kozarsky and J. M. Wilson, *Curr.*

Opin. Genet. Dev., 3:499–503 (1993). The DNA sequences of a number of adenovirus types are available from Genbank, including type Ad5 [Genbank Accession No. M73260]. The adenovirus sequences may be obtained from any known adenovirus type, including the presently identified 41 human types [Horwitz et al, Virology, 2d ed., B. N. Fields, Raven Press, Ltd., New York (1990)]. A variety of adenovirus strains are available from the American Type Culture Collection, Manassas, Va., or available by request from a variety of commercial and institutional sources. In the following embodiment, an adenovirus type 5 (Ad5) is used for convenience.

The selection of the virus useful for engineering the recombinant vectors, including the viral type, e.g., adenovirus, and strain is not anticipated to limit the following invention.

Similarly, selection of the transgene contained within the viral vector is not a limitation of this invention. This method is anticipated to be useful with any transgene. Suitable transgenes for delivery to a patient in a viral vector for gene therapy may be selected by those of skill in the art. These therapeutic nucleic acid sequences typically encode products for administration and expression in a patient in vivo or ex vivo to replace or correct an inherited or non-inherited genetic defect or treat an epigenetic disorder or disease. Such therapeutic genes which are desirable for the performance of gene therapy include, without limitation, a very low density lipoprotein receptor gene (VLDL-R) for the treatment of familial hypercholesterolemia or familial combined hyperlipidemia, the cystic fibrosis transmembrane regulator gene (CFTR) for treatment of cystic fibrosis, DMD Becker allele for treatment of Duchenne muscular dystrophy, and a number of other genes which may be readily selected by one of skill in the art to treat a particular disorder or disease. Thus, the selection of the transgene is not considered to be a limitation of this invention, as such selection is within the knowledge of those skilled in the art.

The viral vector bearing a therapeutic gene may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The viral vector is administered in sufficient amounts totransfect the desired cells and provide sufficient levels of transduction and expression of the selected transgene to provide a therapeutic benefit without undue adverse or with medically acceptable physiological effects which can be determined by those skilled in the medical arts. Conventional and pharmaceutically acceptable routes of administration include direct delivery to the target organ, tissue or site, intranasal, intravenous, intramuscular, subcutaneous, intradermal, oral and other parental routes of administration. Routes of administration may be combined, if desired.

Dosages of the viral vector will depend primarily on factors such as the condition being treated, the selected gene, the age, weight and health of the patient, and may thus vary among patients. For example, a therapeutically effective human dosage of the viral vectors is generally in the range of from about 20 to about 50 ml of saline solution containing concentrations of from about $1\times10^7$ to $1\times10^{10}$ pfu/ml viruses. A preferred adult human dosage is about 20 ml saline solution at the above concentrations. The dosage will be adjusted to balance the therapeutic benefit against any side effects. The levels of expression of the selected gene can be monitored to determine the selection, adjustment or frequency of dosage administration.

III. The Method of the Invention

The method of this invention involves the co-administration of the selected immune modulator with the selected recombinant viral vector. The co-administration occurs so that the immune modulator and vector are administered within a close time proximity to each other. It is presently preferred to administer the modulator concurrently with or no longer than one to three days prior to the administration of the vector. The immune modulator may be administered separately from the recombinant vector, or, if desired, it may be administered in admixture with the recombinant vector.

As illustrated by the examples below, the immune modulator, whether it is an anti-CD40L antibody, anti-CD4 antibody or cytokine, is desirably administered in close time proximity to the administration of the viral vector-used for gene therapy. Particularly, administration of IL-12 or IFN-γ causes reduction in $T_{H2}$ cell levels for about 2–3 days. Therefore, IL-12 and/or IFN-γ are desirably administered within a day of the administration of the viral vector bearing the gene to be delivered. Preferably, however, the IL-12 and/or IFN-γ are administered essentially simultaneously with the viral vector.

The immune modulator may be administered in a pharmaceutically acceptable carrier or diluent, such as saline. For example, when formulated separately from the viral vector, the immune modulator is desirably suspended in saline solution. Such a solution may contain conventional components, e.g. pH adjusters, preservatives and the like. Such components are known and may be readily selected by one of skill in the art.

Alternatively, the immune modulator may be itself administered as DNA, either separately from the vector or admixed with the recombinant vector bearing the transgene. Methods exist in the art for the pharmaceutical preparation of the modulator as protein or as DNA [See, e.g., J. Cohen, Science, 259:1691–1692 (1993) regarding DNA vaccines]. Desirably, the immune modulator is administered by the same route as the recominant vector.

The immune modulator may be formulated directly into the composition containing the viral vector administered to the patient. Alternatively, the immune modulator may be administered separately, preferably shortly before or after administration of the viral vector. In another alternative, a composition containing one immune modulator, such as IL-12, may be administered separately from a composition containing a second immune modulator, such as anti-CD40L antibody, and so on depending on the number of immune modulators administered. These administrations may independently be before, simultaneously with, or after administration of the viral vector.

The administration of the selected immune modulator may be repeated during the treatment with the recombinant viral vector carrying the transgene during the period of time that the transgene is expressed (as monitored by assays that detect transgene expression or its intended effect), or with every booster of the recombinant vector. Alternatively, each re-injection of the same viral vector may employ a different immune modulator.

One advantage of the method of this invention is that it represents a transient manipulation, necessary only at the time of administration of the gene therapy vector. This strategy is anticipated to be safer than strategies based on induction of tolerance, which may permanently impair the ability of the recipient to respond to viral infections.

Furthermore, the preferred use of immune modulators such as the above-mentioned cytokines or antibodies is anticipated to be safer than the use of agents such as cyclosporin or cyclophosphamide (which cause generalized immune suppression) because the transient immune modulation is selective (i.e., CTL-mediated responses are retained, as are humoral responses dependent on $T_{H1}$ function).

In one example of efficient gene transfer according to the methods of this invention, the selected immune modulators are IL-12, which causes the selective induction of $T_{H1}$ cells, and/or IFN-γ, which suppresses induction of $T_{H2}$ cells. Another preferred immune modulator is the anti-CD4$^+$ antibody, GK1.5, which depletes the $T_{H1}$ cells and reduces CTL elimination of the vector. Yet another preferred immune modulator is the anti-CD40 ligand monoclonal antibody, MR1, available from the American Type Culture Collection, Manassas, Va.

As exemplified below, the use of the above-identified immune modulators permitted efficient gene transfer, as well as repeated use of the same viral vector. In conjunction with gene therapy which utilized an adenovirus vector containing either an alkaline phosphatase ("ALP") transgene, a beta-galactosidase ("lacZ") transgene, or a low density lipoprotein receptor ("LDLR") transgene.

The following examples illustrate the preferred methods for preparing-suitable viral vectors useful in the gene therapy methods of the invention. These examples are illustrative only and do not limit the scope of the invention.

EXAMPLE 1
Construction and Purification of Exemplary Recombinant Adenovirus Vectors The recombinant adenovirus H5.010CMVlacZ, was constructed as follows. The plasmid pAd.CMVlac [described in Kozarsky et al, *J. Biol. Chem.*, 269(18):13695–13702 (1994)], which contains adenovirus map units 0–1, followed by a cytomegalovirus enhancer/promoter [Boshart et al, *Cell*, 41:521–530 (1985)], an *E. coli* beta-galactosidase gene (lacZ), a polyadenylation signal (pA), adenovirus 5 map units 9.2–16 (Ad 9.2–16) and generic plasmid sequences including an origin of replication and ampicillin resistance gene was used. pAd.CMVlacZ was linearized with NheI and co-transfected into 293 cells [ATCC CRL1573] with sub360 DNA (derived from adenovirus type 5) which had been digested with XbaI and ClaI as previously described [K. F. Kozarsky, *Somatic Cell Mol. Genet.*, 19:449–458 (1993) and Kozarsky (1994), cited above]. The resulting recombinant virus, H5.010CMVlacZ, contains adenovirus map units 0–1, followed by a CMV enhancer/promoter, a lacZ gene, a polyadenylation signal (pA), adenovirus map units 9.2–100, with a small deletion in the E3 gene at 78.5 to 84.3 mu from the Ad 5 sub360 backbone. The recombinant adenovirus H5.010CBALP contains the adenovirus map units 0–1, followed by a CMV enhanced, chicken cytoplasmic β-actin promoter [T. A. Kost et al, *Nucl. Acids Res.*, 11(23):8287 (1983)], a human placental ALP gene, a polyadenylation signal (pA), and adenovirus type 5 map units 9–100, with a small deletion in the E3 gene at 78.5 to 84.3 mu from the Ad 5 sub360 backbone. This recombinant adenovirus was constructed substantially similarly to the H5.010CMVlacZ adenovirus described above. See, also, Kozarsky (1994), cited above.

These recombinant adenoviruses, H5.010CMVlacZ and H5.010CBALP, were isolated following transfection [Graham, *Virol.*, 52:456–467 (1974)], and were subjected to, two rounds of plaque purification. Lysates were purified on two sequential cesium chloride density gradients as previously described [Englehardt et al, *Proc. Natl. Acad. Sci. USA*, 88:11192–11196 (1991)]. Cesium chloride was removed by passing the virus over BioRad DG10 gel filtration columns using phosphate-buffered saline (PBS).

For mouse experiments, virus was either used fresh, or after column purification, glycerol was added to a final concentration of 10% (v/v), and virus was stored at −70° C. until use.

EXAMPLE 2
Enhancement of Adenovirus Mediated Gene Transfer upon Second Administration by IL-12 and IFN-γ in Mouse Lung The recombinant adenoviruses H5.010CMVlacZ and H5.010CBALP were used in this example. Each virus expresses a different reporter transgene whose expression can be discriminated from that of the first reporter transgene.

Female C57BL/6 mice (6~8 week old) were infected with suspensions of H5.010CBALP ($1\times10^9$ pfu in 50 μl of PBS) via the trachea at day 0 and similarly with H5.010CMVlacZ at day 28. One group of such mice was used as a control. Another group of mice were acutely depleted of CD4$^+$ cells by i.p. injection of antibody to CD4$^+$ cells (GK1.5; ATCC No. TIB207, 1:10 dilution of ascites) at the time of the initial gene therapy (days −3, 0, and +3). A third group of mice was injected with IL-12 (1 μg intratracheal or 2 μg, i.p. injections) at the time of the first administration of virus (days 0 and +1). A fourth group of mice was injected with gamma interferon. (1 μg intratracheal or 2 μg, i.p. injections) at the time of the first administration of virus (days 0 and +1).

When mice were subsequently euthanized and necropsied at days 3, 28, or 31, lung tissues were prepared for cryosections, while bronchial alveolar lavage (BAL) and mediastinal lymph nodes (MLN) were harvested for immunological assays.

A. Cryosections

The lung tissues were evaluated for ALP expression at day 3 and day 28 by histochemical staining following the procedures of Yang I, cited above. β-galactosidase expression was assayed at day 31 by X-gal histochemical staining. The results described below were obtained from the alkaline phosphatase histochemical stains (magnification ×100) or β-galactosidase X-gal stains (magnification ×100).

Instillation of ALP virus ($10^9$ pfu) into the airway of all groups of the C57BL/6 mice resulted in high level transgene expression in the majority of conducting airways that diminished to undetectable levels by day 28. Loss of transgene expression was shown to be due to CTL-mediated elimination of the genetically modified hepatocytes [Yang I, cited above]. In the control mice, no recombinant gene expression was detected three days after the second administration of virus, i.e., at day 31.

Administration of virus to the CD4$^+$-depleted animals was associated with high level recombinant transgene expression that was stable for a month. Expression of the second virus was detectable on day 31. Thus, depletion of the CD4$^+$ cells effectively permits readministration of the vector without immediate CTL elimination.

Initial high level gene transfer diminished after about one month in the IL-12 treated mice. However, in contrast to the control, high level gene transfer to airway epithelial cells was achieved when virus was readministered to IL-12 treated animals at day 28, as seen in the day 31 results.

The gamma-interferon treated animals were virtually indistinguishable from the animals treated with IL-12 in that efficient gene transfer was accomplished upon a second administration of virus.

Thus, the use of these cytokines as immune modulators enabled the repeated administration of the vector without its immediate elimination by neutralizing antibody. In other experiments, $T_{H2}$ cells were not inhibited at the expense of increased $T_{H1}$ activation. In mice treated with the ALP virus parenterally and IL-12 i.p., the IL-12 did not increase adenovirus-specific CTL activity as shown by chromium release assays. More importantly, treatment of the animals with IL-12 at the time of intratracheal instillation of virus did not enhance inflammation or diminish transgene persistence following a second administration of virus.

B. Immunological Assays—MLN

Lymphocytes from MLN of the control group and IL-12 treated group of C57BL/6 mice were harvested 28 days after administration of H5.010CBALP and restimulated in vitro with UV-inactivated H5.010CMVlacZ at 10 particles/cell for 24 hours. Cell-free supernatants were assayed for the presence of IL-2 or IL-4 on HT-2 cells (an IL-2 or IL-4-dependent cell line) [Yang I, cited above]. Presence of IFN-γ in the same lymphocyte culture supernatant was measured on L929 cells as described [Yang I, cited above]. Stimulation index (S.I.) was calculated by dividing $^3$H-thymidine cpm incorporated into HT-2 cells cultured in supernatants of lymphocytes restimulated with virus by $^3$H-thymidine cpm incorporated into HT-2 cells cultured in supernatants of lymphocytes incubated in antigen-free medium.

The results are shown in Table I below.

TABLE I

| | $^3$H-Thymidine Incorporation (cpm ± SD) | | | |
|---|---|---|---|---|
| | Medium | H5.010CMVlacZ | S.I. | IFN-γ titre (IU/ml)$^d$ |
| C57BL/6 | 175 ± 40 | 2084 ± 66 | 11.91 | 80 |
| anti-IL2 (1:5000) | | 523 ± 81 | 2.98 | |
| anti-IL4 (1:5000) | | 1545 ± 33 | 8.83 | |
| C57BL/6 + IL12 | 247 ± 34 | 5203 ± 28 | 21.07 | 160 |
| anti-IL2 (1:5000) | | 776 ± 50 | 3.14 | |
| anti-IL4 (1:5000) | | 4608 ± 52 | 18.66 | |

Stimulation of lymphocytes from regional lymph nodes with both recombinant adenoviruses led to secretion of cytokines specific for the activation of both $T_{H1}$ (i.e., IL-2 and IFN-γ) and $T_{H2}$ (i.e., IL-4) subsets of T helper cells (Table I).

Analysis of lymphocytes from the IL-12 treated animals stimulated in vitro with virus revealed an increased secretion of IL-2 and IFN-γ relative to the production of IL-4, when compared with animals that did not receive IL-12 (i.e., ratio of IL-2/IL-4 was increased from 3 to 6 when IL-12 was used; Table I).

C. Immunological Assays—BAL

BAL samples obtained from animals 28 days after primary exposure to recombinant virus were evaluated for neutralizing antibodies to adenovirus and anti-adenovirus antibody isotypes as follows. The same four groups of C57BL/6 mice, i.e., control, CD4$^+$ depleted, IL-12 treated and IFN-γ treated, were infected with H5.010BALP. Neutralizing antibody was measured in serially-diluted BAL samples (100 µl) which were mixed with H5.010CBlacZ ($1\times10^6$ pfu in 20 µl), incubated for 1 hour at 37° C., and applied to 80% confluent Hela cells in 96 well plates ($2\times10^4$ cells per well). After 60 minutes of incubation at 37° C., 100 µl of DMEM containing 20% FBS was added to each well. Cells were fixed and stained for β-galactosidase expression the following day.

All cells were lacZ positive in the absence of anti-adenoviral antibodies.

Adenovirus-specific antibody isotype was determined in BAL by using an enzyme-linked immunosorbent assay (ELISA). Briefly, 96-well plates were coated with 100 µl of PBS containing $5\times10^9$ particles of H5.010CBlacZ for 18 hours at 4° C. The wells were washed 5 times with PBS. After blocking with 200 µl of 2% BSA in PBS, the plates were rinsed once with PBS and incubated with 1:10 diluted BAL samples for 90 minutes at 4° C. Thereafter, the wells were extensively washed and refilled with 100 µl of 1:1000 diluted ALP-conjugated anti-mouse IgG or IgA (Sigma). The plates were incubated, subsequently washed 5 times, and 100 µl of the substrate solution (p-nitrophenyl phosphate, PNPP) was added to each well. Substrate conversion was stopped by the addition of 50 µl of 0.1M EDTA, and reactions were read at 405 nm.

Figure 1B:
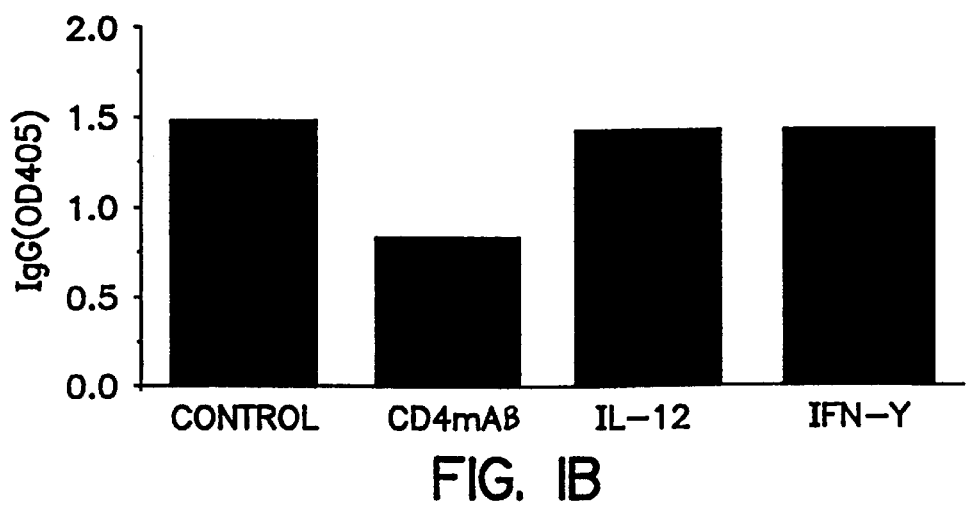
FIG. 1B is a graph summarizing the relative amounts (OD$_{405}$) of IgG present in BAL samples. The symbols are as described in FIG. 1A.
Figure 1C:
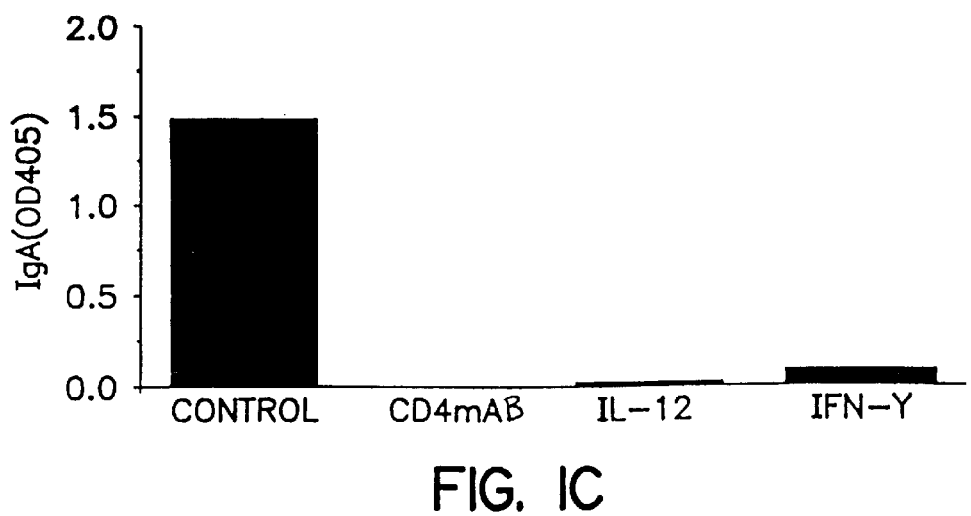
FIG. 1C is a graph summarizing the relative amounts ($OD_{405}$) of IgA present in BAL samples. The symbols are as described in FIG. 1A.

The results are shown graphically in FIGS. 1A through 1C, which summarize neutralizing antibody titer, and the relative amounts ($OD_{405}$) of IgG and IgA present in BAL samples. The titer of neutralizing antibody for each sample was reported as the highest dilution with which less than 50% of cells stained blue.

As demonstrated in the first bar of FIGS. 1A through 1C, the cytokines identified in Table 1 above were associated in the control mice with the appearance of antibodies to adenovirus proteins in BAL of both the IgG and IgA isotypes that were capable of neutralizing the human Ad5 recombinant vector in an in vitro assay out to a 1:800 dilution.

As shown in the second bar of the graphs of FIGS. 1A through 1C, transient CD4$^+$ cell depletion inhibited the formation of neutralizing antibody (FIG. 1A) and virus specific IgA antibody (FIG. 1C) by 80-fold, thereby allowing efficient gene transfer to occur following a second administration of virus. FIG. 1B shows a slight inhibition of IgG as well.

As shown in the third bar of the three graphs, IL-12 selectively blocked secretion of antigen specific IgA (FIG. 1C), without significantly impacting on formation of IgG (FIG. 1B). This was concurrent with a 20-fold reduction in viral-specific neutralizing antibody (FIG. 1A).

The gamma-interferon treated animals (fourth bar of FIGS. 1A and 1B) were virtually indistinguishable from the animals treated with IL-12 in that virus specific IgA (FIG. 1C) and neutralizing antibody (FIG. 1A) were decreased as compared to the control animals not treated with cytokine, but not to the extent obtained with those treated with IL-12.

These studies demonstrate that the administration of selected immune modulators to recipients of gene therapy recombinant viral vectors at or about the time of primary exposure to the vector can prevent the formation of blocking antibodies and/or CTL elimination of the vector both initially and at the time of repeated exposure to the viral vector. The concordant reduction of neutralizing antibody with antiviral IgA suggests that immunoglobulin of the IgA subtype is primarily responsible for the blockade to gene transfer.

EXAMPLE 3

Enhancement of Adenovirus Mediated Gene Transfer upon Second Administration by IL-12 and IFN-γ in Mouse Liver Experiments substantially identical to those described in Example 2 above were conducted in which viral vectors were administered into the blood for introduction of the transgene into the liver (rather than intratracheal delivery into the lung).

The recombinant adenoviruses H5.010CMVlacZ and H5.010CBALP were used in this example.

Female C57BL/6 mice (6–8 weeks old) were injected with suspensions of H5.010CBALP ($1\times10^9$ pfu in 50 µl of PBS) i.p. at day 0 and similarly with H5.010CMVlacZ at day 28. One group of such mice was used as a control. Another group of mice was acutely depleted of CD4$^+$ cells by i.p. injection of antibody to CD4$^+$ cells (GK1.5; ATCC No. TIB207, 1:10 dilution of ascites) at the time of the initial gene therapy (days −3, 0, and +3). A third group of mice was injected with IL-12 (2 μg, i.p. injections) at the time of the first administration of virus (days 0 and +1). A fourth group of mice was injected with gamma interferon (2 μg, i.p. injections) at the time of the first administration of virus (days 0 and +1).

When mice were subsequently euthanized and necropsied at days 3, 28, or 31, liver tissues were prepared for cryo-sections according to the procedures used above for lung tissue in Example 2.

The cryosection results were substantially similar for liver-directed gene therapy according to this method as for the lung-directed therapy of Example 2 above. The results described below were obtained from the alkaline phosphatase histochemical stains (magnification ×100) or β-galactosidase X-gal stains (magnification ×100).

Administration of ALP virus ($10^9$ pfu) into the veins of all groups of the C57BL/6 mice resulted in high level transgene expression in liver tissue that diminished to undetectable levels by day 28. Loss of transgene expression was shown to be due to CTL mediated elimination of the genetically modified hepatocytes [see also, Yang I, cited above].

In the control mice, no recombinant gene expression was detected three days after the second administration of virus, i.e., day 31.

Administration of virus to the CD4$^+$ depleted animals was associated with substantially lower neutralizing antibodies and high level recombinant transgene expression that was stable for a month. Expression of the second virus was detectable on day 31.

Initial high level gene transfer diminished after about one month in the IL-12 treated mice; however, in contrast to the control, some gene transfer to the liver via the blood was achieved when virus was readministered to IL-12 treated animals at day 28 and the level of neutralizing antibody was reduced.

The gamma-interferon treated animals were virtually indistinguishable from the animals treated with IL-12 in that efficient gene transfer was accomplished upon a second administration of virus.

Thus, the use of these cytokines and the anti-CD4$^+$ antibodies as immune modulators enabled the repeated liver-directed administration of the vector without its immediate elimination by neutralizing antibodies.

EXAMPLE 4
Adenovirus Mediated Gene Transfer in Mouse Liver

Immune responses to primary administration of recombinant virus were characterized further using different strains of mice.

Recombinant virus (H5.010CMVLacZ or H5.010CBALP) was inactivated with ultraviolet light in the presence of 8-methoxypsoralen. Briefly, purified virus was resuspended in 0.33 mg/ml of 8-methoxypsoralen solution and exposed to a 365 nm UV light source on ice at 4 cm from the lamp filter for 30 min. The virus was then passed over a Sephadex G-50 column equilibrated with PBS. Limiting dilution transduction assays of inactivated stocks of virus demonstrated less than one functional virus per $10^5$ particles of inactivated virus. Suspensions of the viruses ($2 \times 10^9$ pfu in 100 μl of PBS) were infused into the tail vein of 6 to 8 week old female mice as etailed in the following experiments. Each experiment was performed with a minimum of three mice in which transgene expression was quantified in a section of each of 5 lobes. The minimum analysis was 15 sections per experimental condition.

a. C57BL/6 mice [H-$2^b$; Jackson Laboratories, Bar Harbor, Me.] were injected with suspensions of H5.010CMVlacZ at day 0 and similarly with H5.010CBALP at day 28 ("B6 mice");

b. C57BL/6 mice were injected with UV-inactivated H5.010CMVlacZ at day 0 and H5.010CBALP at day 28 ("B6-UV mice");

c. MHC class II-deficient (II$^-$) mice [GenPharm International, Mountain View, Calif.], bred into the C57BL/6 background (between 5–10 generations) and which carry the H-$2^b$ haplotype, are unable to express I-A$^b$ determinants and cannot develop CD4$^+$ T cell mediated responses [Grusby et al, *Science*, 253:1417–1420 (1991)]. These mice were infected with H5.010CBALP at day 0 and H5.010CMVlacZ at day 28 ("class II$^-$ mice");

d. β2 microglobulin deficient (β2m$^-$) mice [GenPharm International, Mountain View, Calif.], bred onto the C57BL/6 background (between 5–10 generations) and which carry the H-$2^b$ haplotype are unable to develop MHC class I associated responses. These mice were infected with H5.010CMVlacZ at day 0 and H5.010CBALP at day 28 ("β2$^-$ mice");

e. C57BL/6 mice were inoculated i.p. with 0.5 ml aliquots of 1:10 dilution of mouse ascites fluid containing the GK1.5 (anti-CD4 Mab, ATCC TIB207) at days −3, 0 and +3 as described in Example 2. This was equivalent to 100 μg of purified monoclonal antibody per injection. These CD4$^+$ cell-depleted mice were infected with H5.010CMVlacZ at day 0 and H5.010CBALP at day 28 ("CD4Ab mice"); and f. C57BL/6 mice, treated with IL-12 (2 μg in 200 μl PBS) i.p. on day 0 and day +1 as described in Example 2, were infected with H5.010CMVlacZ at day 0 and H5.010CBALP at day 28 ("IL-12 mice").

Mice from each group were subsequently euthanized and liver tissues evaluated for lacZ expression by X-gal histochemistry (magnification ×100) at day 3 and day 28; and for ALP expression by histochemical staining at day 31 (magnification ×100). Development of neutralizing antibody to adenovirus in each group of mice was examined in serum samples obtained at day 28.

Figure 2:
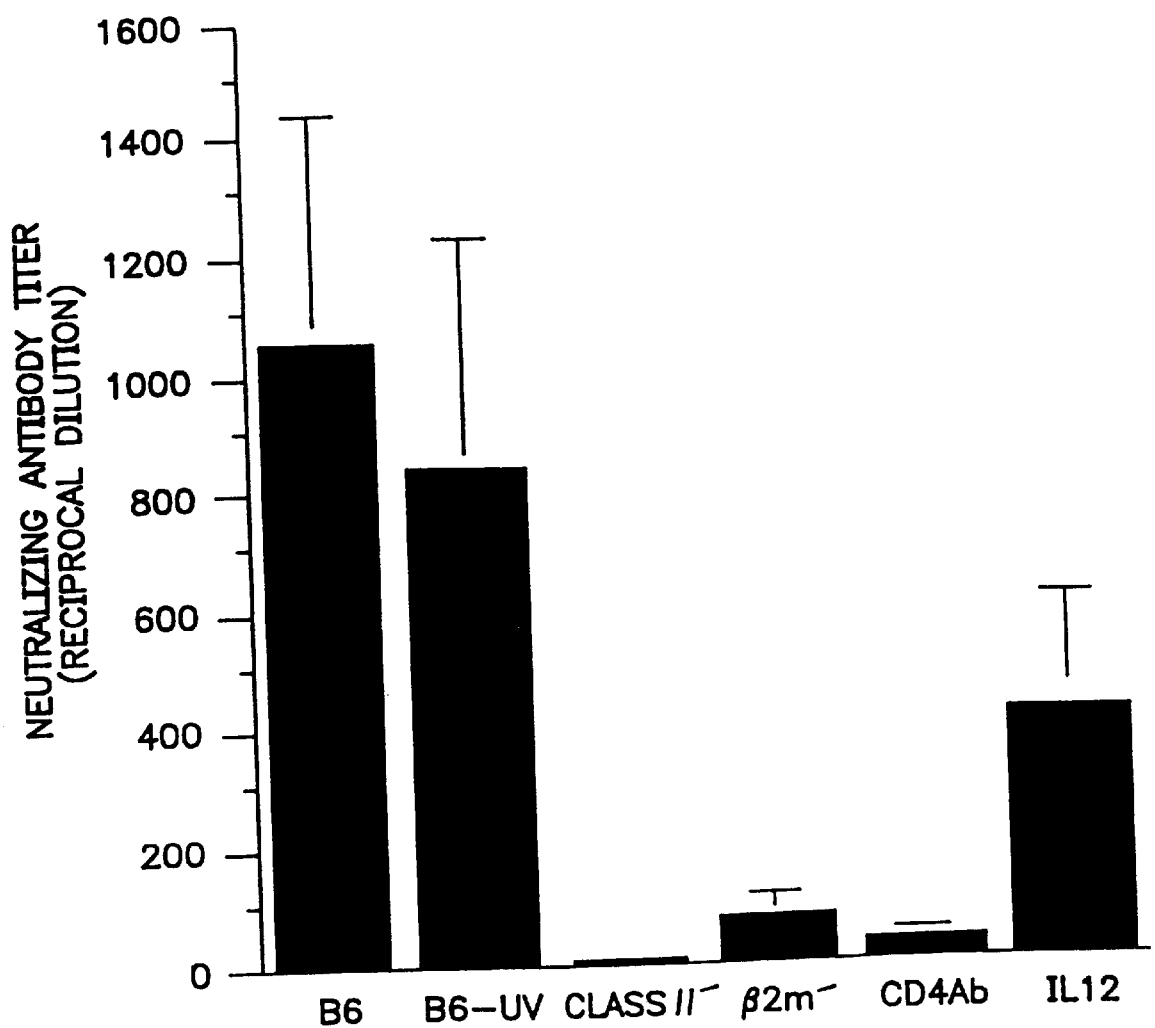
FIG. 2 is a graph simmarizing neutralizing antibody titer, expressed as reciprocal dilution of serum samples for the animals of Example 4. The symbols representing the mice are described as follows: C57BL-6 mice infected with H5.010CMVlacZ on day 0 and with H5.010CBALP at day 28 ("B6 mice"); C57BL-6 mice infected with UV-inactivated H5.010CMVlacZ on day 0 and with H5.010CBALP at day 28 ("B6-UV mice"); MHC class II-deficient mice infected with H5.010CMVlacZ at day 0 and with H5.010CBALP on day 28 ("class II$^-$ mice"); β2 microglobulin deficient mice infected with H5.010CMVlacZ at day 0 and with H5.010CBALP at day 28 ("β2m$^-$ mice"); and C57BL/6 mice treated with GK1.5 (anti-CD4) mAb and infected with H5.010CMVlacZ at day 0 and with H5.010CBALP at day 28 ("CD4Ab mice").

Infusion of lacz virus into C57BL/6 mice was associated with high level, but transient, expression of the reporter gene and the eventual development of neutralizing antibody directed against adenoviral antigen (FIG. 2). No gene transfer was detected when the ALP virus was subsequently infused into these animals. In contrast, the class II$^-$ mice did not produce neutralizing antibody (FIG. 2) and were receptive to high level gene transfer from a second administration of virus. Similarly, animals transiently depleted of CD4 partially stabilized lacZ expression and did not develop neutralizing antibody,, allowing efficient readministration of virus.

In the B6-UV mice which received UV-inactivated recombinant virus, the inactivated virus generated a full neutralizing antibody response (FIG. 2) that completely prevented subsequent gene transfer. This result demonstrates that capsid proteins of the input virus are sufficient to activate a blocking T helper cell and B cell-mediated humoral immune response.

The experiment with β2m$^-$ mice was performed to evaluate the role of CD8 cells and class I MHC expression in the primary response to virus [Zijlstra et al, *Nature*, 344:742–746 (1990)]. Transgene expression was stable in these animals consistent with prior reported data [Yang III, cited above]. However, gene transfer occurred at a significant level in the setting of a readministration of virus. This was unexpected because this strain of mice should have all components of the immune response necessary to produce neutralizing antibody, (i.e., CD4 cells, MHC class II expression and B cells). These animals failed to mount a significant neutralizing antibody response to adenoviral antigens. These results suggest dysregulation of T helper and/or B cell activation (FIG. 2).

Analysis of lymphocytes from β2m- animals demonstrated antigen-activated secretion of IFN-γ in excess of that measured in C57BL/6 mice, possibly due to the persistence of virus-infected cells and the chronic activation of $T_{H1}$ cells. The amplified $T_{H1}$ response in β2m- mice could lead to an inhibition of $T_{H2}$ cells resulting in diminished production of anti-viral antibodies.

Transgene expression was found to be stabilized in animals deficient in CD8 cells and MHC class I.by virtue of a germ line β2m- interruption. Specific ablation of perforin, the molecule on CTLs and natural killer (NK) cells that mediates cytolysis, similarly prolongs of transgene expression (data not shown).

EXAMPLE 5
Effect of CD4 Antibody on Ad-mediated Gene Transfer Upon Repeated Administrations Suspensions of the recombinant adenoviruses expressing different transgenes were infused into the tail vein of C57BL/6 ($H-2^b$) mice at 21 day intervals. H5.010CMVLDLR is an adenovirus deleted of the E1a and E1b genes and has a deletion in E3 gene at 78.5 to 84.3 mu from the Ad 5 sub360 backbone, with a LDL receptor gene in place of the E1 deletion [described in Kozarsky et al, *J. Biol. Chem.*, 269:1–8 (1994)].

5.010CMVLDLR was administered at day 0; H5.010CMVlacZ at day 21; and H5.010CBALP at day 42. A control group of mice was administered i.p. injections of saline at days −3, 0 and +3, with respect to each infusion of virus. A second group of mice was given i.p. injections of CD4 depleting antibody to block T helper cell activation (GK1.5 mAb) in the same protocol. A third group of mice was given i.p. injections of GK1.5 mAb at days −3, 0, 3, 18, 21 and 24. A fourth group of mice, which did not receive the initial administration of H5.010CMVLDLR, was treated with GK1.5 mAb at days −3, 0 and 3.

The mice were subsequently euthanized, and the liver tissues were evaluated for LDLR expression by immunohistochemistry at day 3, for lacZ expression by X-gal histochemistry at day 24, and for ALP expression by histochemical staining at day 45. The assays were performed as follows:

A. Immunofluorescent staining for LDLR expression was performed as follows: Frozen sections (6 μm) were fixed in methanol as described in Morris et al, cited above. After blocking with 10% goat serum in PBS (GS/PBS), sections were incubated with a polyclonal antibody to LDLR (1:200) for 60 minutes, and then with goat anti-rabbit IgG-FITC for 30 minutes. Sections were washed and mounted with Citiflour (Citifluor, UK).

B. X-gal histochemistry was performed as follows: Sections of fresh frozen tissue (6 μm) were fixed in 0.5% glutaraldehyde for 10 minutes, rinsed twice for 10 minutes in PBS containing 1 mM $MgCl_2$ and incubated in 1 mg/ml of 5-bromo-4-chloro-3-indolyl β-D-galactopyranoside (X-gal), 5 mm $K_3Fe(CN)_6$, 5 mM $K_4Fe(CN)_6$, and 1 mM $MgCl_2$ in PBS for 3 hours.

C. ALP histochemistry was performed as follows: Frozen sections (6 μm) were fixed in 0.5% glutaraldehyde for 10 minutes, rinsed in PBS, incubated at 65° C. for 30 minutes to inactivate endogenous ALP activity, washed in 100 mM Tris (pH 9.5), 100 mM NaCl and 50 mM $MgCl_2$, and stained in the same buffer containing 0.165 mg/ml of 5-bromo-4-chloro-3-indolyl phosphate (BCIP) and 0.33 mg/ml Nitroblue Thetrazolium (NBT) at 37° C. for 30 minutes.

The results discussed below were obtained from analyses of the cytochemical stains of liver tissue three days after each virus infusion, including LDLR virus on day 0, lacZ virus on day 21 and ALP virus on day 42 (magnification ×150).

Serum samples were also collected at days 0, 3, 7, 14, 21, 28, 35 and 42 from each group of animals and assayed for neutralizing antibody titer. Serum samples were incubated at 56° C. for 30 minutes and then diluted in DMEM in twofold steps starting from 1:20. Each serum dilution (100 μl) was mixed with H5.010CMVlacZ ($2 \times 10^6$ pfu in 20 μl), incubated for 1 hour at 37° C., and applied to 80% confluent Hela cells in 96-well plates ($2 \times 10^4$ cells per well). After 60 minutes incubation at 37° C., 100 μl of DMEK containing 20% FBS were added to each well. Cells were fixed and stained for β-galactosidase expression on the following day. All of the cells stained blue in the absence of serum samples. The titer of neutralizing antibody for each sample was reported as the highest dilution with which less than 50% of cells stained blue. FIGS. 3A–3D report the antibody titer expressed as a function of days post-infection.

Figure 3B:
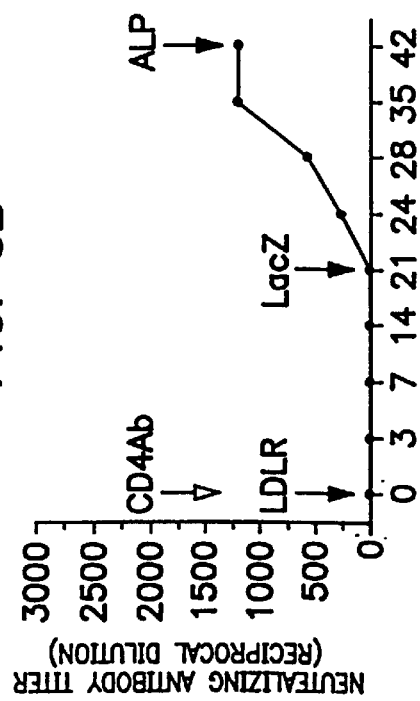
FIG. 3B is a graph similar to that of FIG. 3A for C57BL/6 mice infused into the tail vein on day 0 with H5.010CMVLDLR and on day 21 with H5.010CMVLacZ, and on day 42 with H5.010CBALP, and administered with anti-CD4 mAb GK1.5 on days –3, 0 and 3.
Figure 3D:
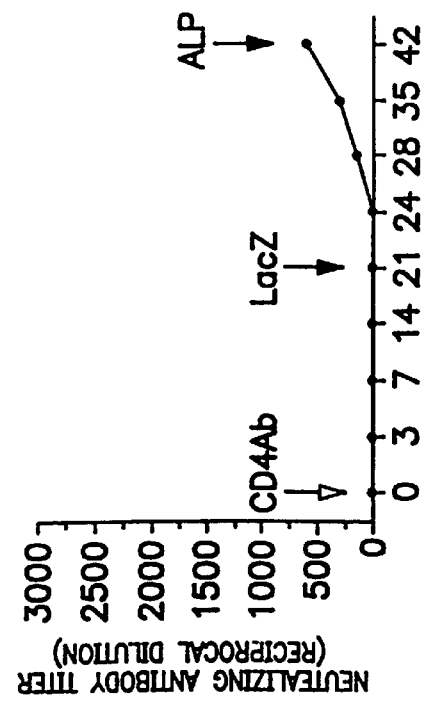
FIG. 3D is a graph similar to that of FIG. 3A for C57BL/6 mice infused into the tail vein on day 21 with H5.010CMVLacZ, and on day 42 with H5.010CBALP, and administered with anti-CD4 mAb GK1.5 on days –3, 0, and 3.

These experiments demonstrated that in the group of mice receiving no CD4 antibodies, efficient gene transfer occurred following the first virus. However, the development of neutralizing antibody blocked gene transfer with the subsequent two viruses. Neutralizing antibody rapidly appeared in serum following the second virus if CD4 antibodies were not coadministered (FIG. 3B). The third virus was not effective in these animals. In contrast, administration of CD4 antibodies at the time of first infusion of virus prevented the formation of neutralizing antibodies (FIG. 3B) and allowed high level gene transfer with the second virus. The appearance of neutralizing antibody following the second virus was accelerated (FIG. 3B as compared to the time course of a primary response in FIG. 3A), suggesting that activation of some level of cellular immunity does occur even in the presence of CD4 antibodies. Administration of CD4 antibody with the second virus again blocked neutralizing antibody in the group of mice receiving CD4 antibodies and both viruses, allowing efficient gene transfer with the third virus.

These experiments demonstrate that transient immune blockade at the time of virus delivery, as opposed to chronic immune suppression, is all that is necessary for efficient gene transfer.

Figure 3A:
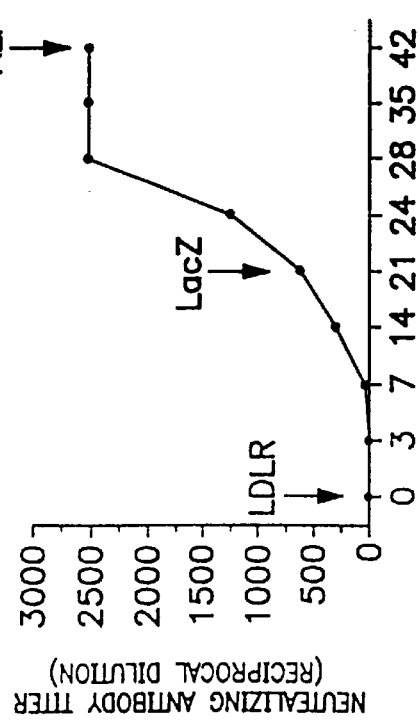
FIG. 3A is a graph summarizing neutralizing antibody titer, expressed as reciprocal dilution of serum samples for C57BL/6 mice infused into the tail vein on day 0 with H5.010CMVLDLR and on day 21 with H5.010CMVLacZ, and on day 42 with H5.010CBALP, and administered with saline on days –3, 0 and 3. The titer is reported as a function of days post-infection.
Figure 3C:
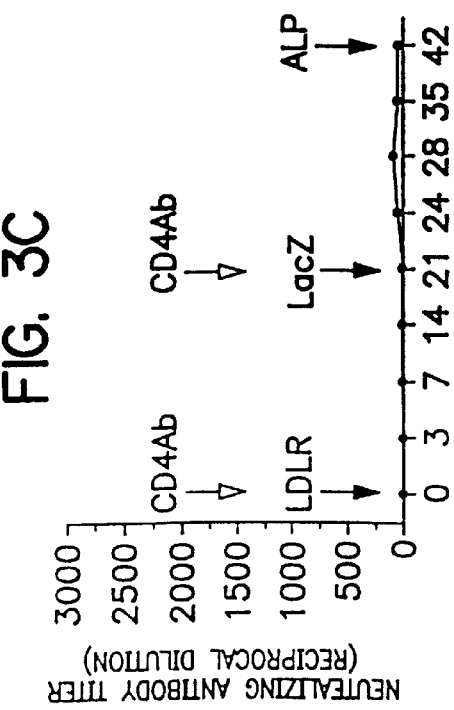
FIG. 3C is a graph similar to that of FIG. 3A for C57BL/6 mice infused into the tail vein on day 0 with H5.010CKVLDLR and on day 21 with H5.010CMVLacZ, and on day 42 with H5.010CBALP, and administered with anti-CD4 mAb GK1.5 on days –3, 0, 3, 18, 21 and 24.

The fourth group of animals received CD4 antibody on day −3 without H5.010CMVLDLR administration, i.e., 21 days prior to primary administration of virus. Neutralizing antibody that developed subsequent to primary challenge of virus blocked gene transfer 21 days later (FIG. 3D) in a manner indistinguishable from that observed in naive animals not pretreated with CD4 antibody (FIG. 3A). This result confirms the transient nature of the CD4 depletion.

EXAMPLE 6
Effect of IL-12 on Ad-specific Antibody Isotypes and CTL Responses

A. Serum samples obtained from the C57BL/6 mice ("B6") and IL-12 treated C57BL/6 ("B6+IL12") mice of Example 5 were tested 28 days after infection for adenovirus-specific IgG1 and IgG2a antibody isotypes.

A solid phase enzyme linked immunosorbent assay (ELISA) using purified H5.010CMVlacZ virus as antigen was performed. Immunolon-2-U microtiter plates (Fisher) were coated with 200 ng/well of viral antigen in 100 ml of PBS for 6 hours at 37° C., washed three times in PBS, and blocked in PBS/1% BSA overnight at 4° C. The following day, 4-fold serial diluted serum samples were added to antigen-coated plates and incubated for 4 hours at 37° C. Plates were washed three times in PBS/1% BSA and incubated with goat anti-mouse IgG1-biotin or goat anti-mouse IgG2a-biotin (CALTAG Laboratories, San Francisco, Calif.) at 1:5000 dilution for 2 hours at 37° C. Plates were washed as above and Avidin-ALP (Sigma) was added to each well at 1:5000 dilution for 1 hour at 37° C. Wells were again washed as above and PNPP substrate was added. Optical densities were read on a Biorad model 450 microplate reader.

Figure 4A:
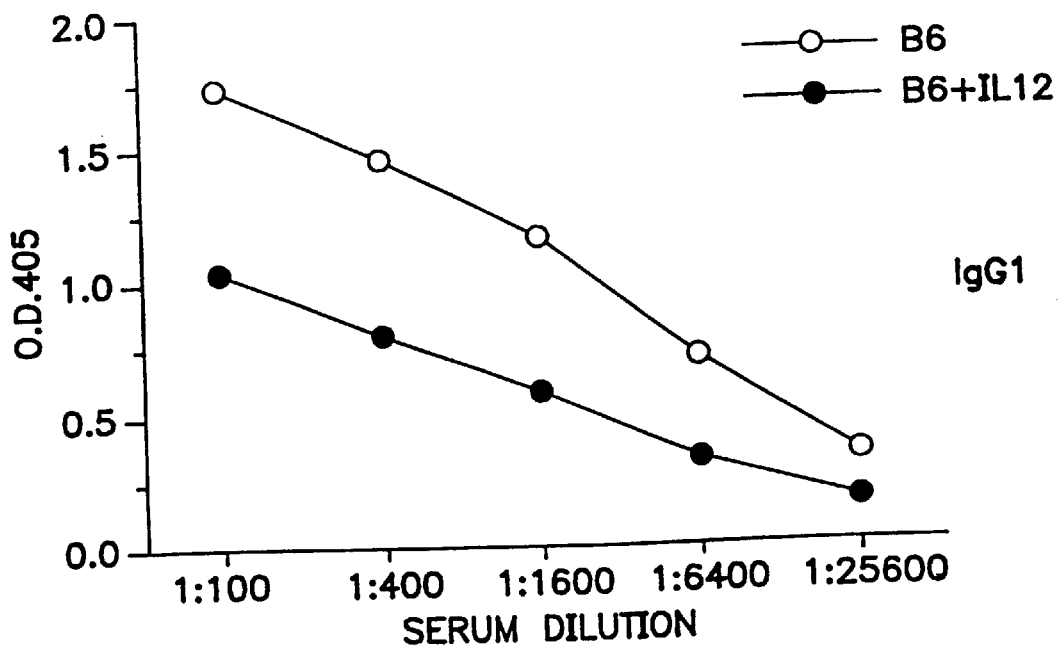
FIG. 4A is a graph summarizing the relative amounts ($OD_{405}$) of IgG1 present in serum samples as a function of sample dilutions, as described in Example 6.
Figure 4B:
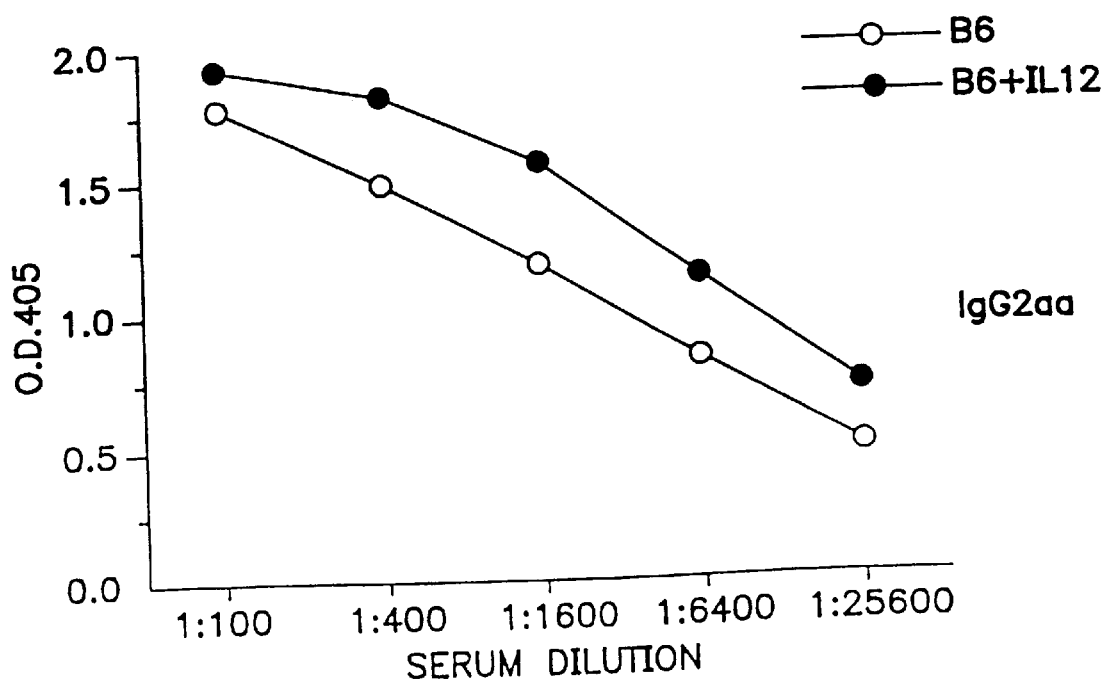
FIG. 4B is a graph summarizing the relative amounts ($OD_{405}$) of IgG2a present in the serum samples as a function of sample dilutions as described in Example 6.

FIGS. 4A and 4B summarize the relative amounts ($OD_{405}$) of IgG1 and IgG2a, respectively, present in serum samples as a function of sample dilutions. The ELISA assays of sera revealed anti-viral antibodies of both IgG1 and IgG2a subtypes consistent with activation of both $T_{H1}$ and $T_{H2}$ subsets, respectively. Animals receiving IL-12 produced less anti-viral IgG1 at the expense of an increased production of IgG2a.

B. Splenocytes harvested from C57BL/6 mice ("B6") and IL-12-treated C57BL/6 mice ("B6+IL12") of Example 5 were restimulated in vitro 10 days after administration of H5.010CBALP with H5.010CMVlacZ for 5 days in DMEM supplemented with 5% FBS and 50 mM 2-mercaptoethanol. These cells were tested for specific lysis on mock-infected ("mock") and H5.010CBALP ("ALP")-infected C57SV cells in a 6 hour $^{51}$Cr release assay performed subsequently using the following ratios of effector to target cells (c57SV, H-$2^b$) in 200 μl DMEM with 10% FBS in V-bottom 96-well plates (E:T=50:1, 25:1, 12:1, 6:1, 5:1 and 3:1).

Figure 5:
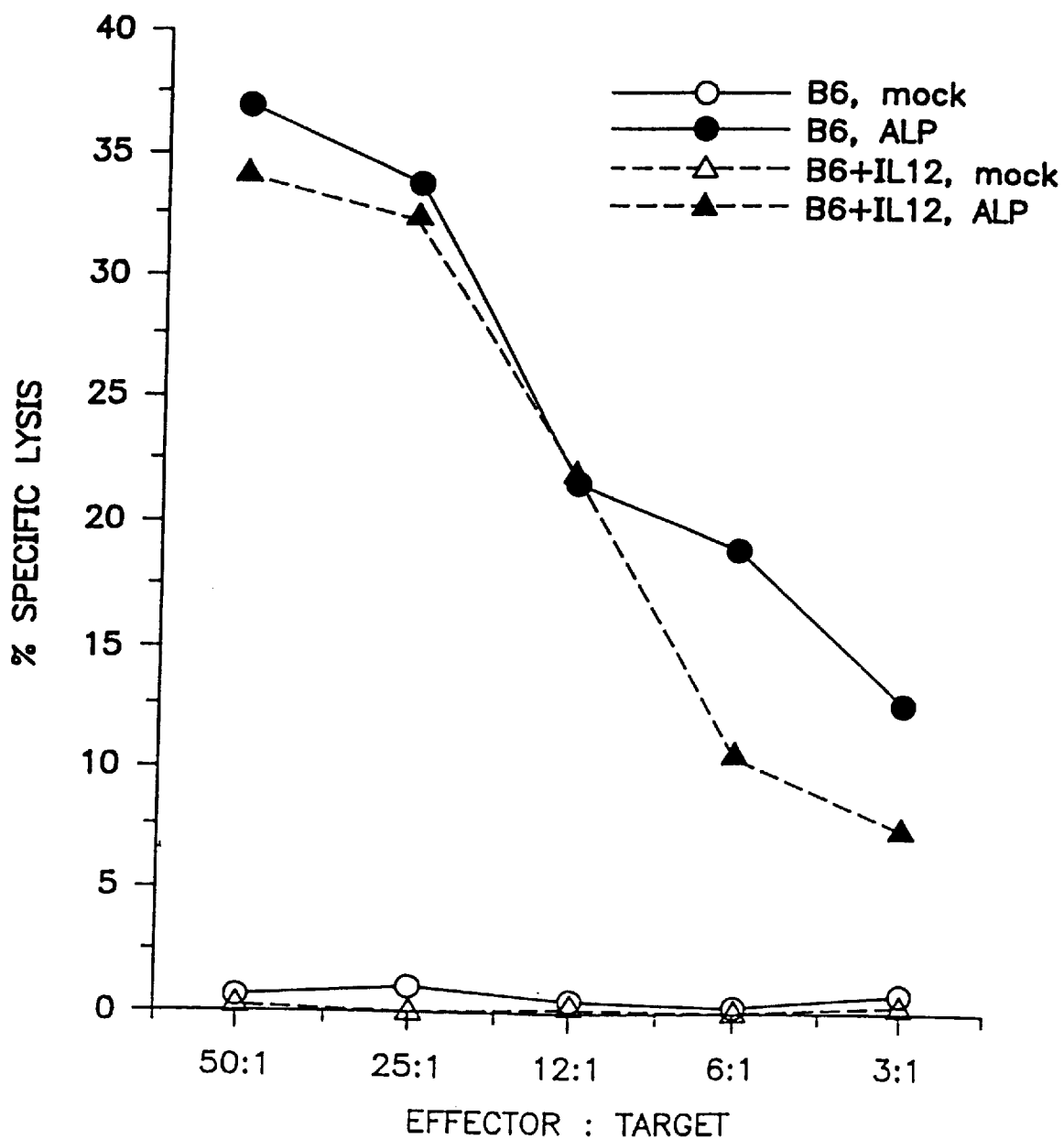
FIG. 5 is a graph illustrating percentage of specific lysis on mock-infected ("mock") and H5.010CBALP ("ALP")-infected C57SV cells as a function of effector to target ratios for a $^{51}$Cr release assay of Example 6B. Splenocytes from C57BL/6 mice ("B6") and IL-12 treated C57BL/6 ("B6+ IL12") mice 10 days after administration of H5.010CBALP, were restimulated in vitro with H5.010CMVlacZ for 5 days.

Prior to mixing with the effector cells, target cells (1×10⁶) were labeled with 100 μCi of $^{51}$Cr after a 24 hr-infection with H5.010CMVlacZ at an moi of 50 and used at 5×10³ cells/well. After incubation for 6 hr, aliquots of 100 μl supernatant were removed for counting in a gamma counter. Percentage of specific $^{51}$Cr release was calculated as: [(cpm of sample−cpm of spontaneous release)/(cpm of maximal release−cpm of spontaneous release)]×100. The results, reported as percentage of specific lysis as a function of different effector to target ratios (FIG. 5), show that CTL activity against virus-infected target cells was unaffected by IL-12 treatment.

The net result was a 3-fold reduction in neutralizing antibody, the magnitude of which was insufficient to allow efficient gene transfer upon readministration of virus. Differences in efficiency of virus readministration between the β2m- mice and the IL-12 treated C57BL/6 mice could reflect inadequate cytokine mediated repression following i.p. injection of IL-12 or mechanisms other than inhibition of $T_{H2}$ activation.

EXAMPLE 7
CD40L-deficient Mice Illustrate the Necessary Role of T Cell Activation in Host Responses to Adenoviral Vectors The role of CD40L mediated signaling of T cells in cellular and humoral immune responses to adenoviral vectors was studied in mice genetically deficient in CD40L. Previous studies have demonstrated abnormalities in thymic dependent B cell responses in these mice [J. Xu et al, *Immunity*, 1:423–431 (1994) and B. Renshaw et al, *J. Exp. Med.*, 180:1889–1900 (1994)]. CD40L-deficient mice (CD40L KO) and their normal litter mates in a C57BL/6–129 chimeric background [J. Xu et al, cited above] were administered lacZ containing E1 deleted adenovirus (H5.010CMVlacZ) on day 0 into the trachea (1×10⁹ in 50 μl of PBS), to effect gene transfer to lung, and into the peripheral circulation via the tail vein (2×10⁹ in 100 μl in PBS), to effect gene transfer to liver. Animals were retreated with H5.010CBALP, an adenoviral vector containing a different reporter gene (alkaline phosphatase, ALP), on day 28. Blood was analyzed prior to the second vector administration for neutralizing antibodies, and tissues were harvested for analysis of reporter gene expression 3 days later (i.e., day 31). Animals were sacrificed 3 and 28 days later to assess the efficiency and stability of transgene expression, respectively. Table II summarizes morphometric analyses of these tissues.

TABLE II

Quantitative Analysis of Mouse Lung and Liver for Efficiency of Transgene Expression

|  | Day 3 | Day 28 | Day 31 |
| --- | --- | --- | --- |
| ¹Lung (% airways >25% transgene exprassion) | | | |
| Control | 76 | 0 | 0 |
| CD40L Ab | 72 | 42 | 30 |
| CD40L KO | 75 | 30 | 45 |
| ²Liver (% transgene expression) | | | |
| Control | 90.5 ± 2.6 | 0 | 0 |
| CD40L Ab | 89.3 ± 3.1 | 46.7 ± 4.8 | 8.2 ± 4.2 |
| CD40L KO | 92.3 ± 4.0 | 60.4 ± 2.8 | 85.9 ± 3.4 |

¹Data were quantified by examining a total of 100 airways from 3 mice for the presence of transgene-containing respiratory epithelial cells using the criteria of a positive airway as the transgene was greater than 25%.
²Data are presented as the mean ± 1 S.D.

Figure 6A:
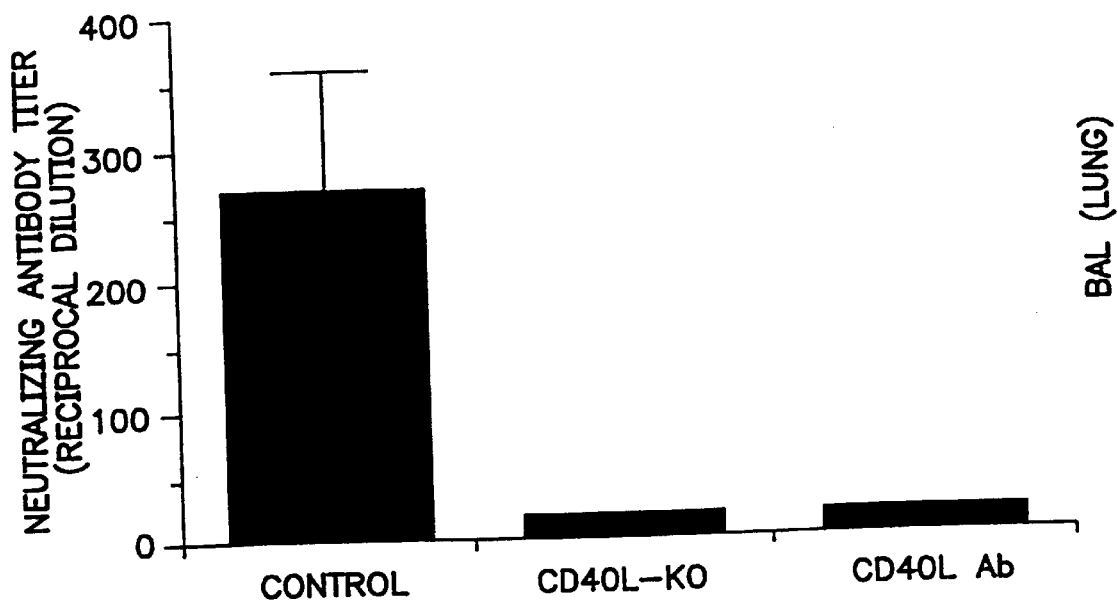
FIG. 6A is a bar chart providing the neutralizing antibodies to Ad5 obtained in the BAL (lung experiment) of Example 7. The results in column 1 are from C57BL/6 mice (control), column 2 results are from CD40L-deficient knock-out mice (CD40L-KO), and column 3 results are from C57BL/6 mice treated with CD40L antibody (CD40L Ab). Data are presented as the mean neutralizing antibody titer of three samples +/–1 S.D.
Figure 6B:
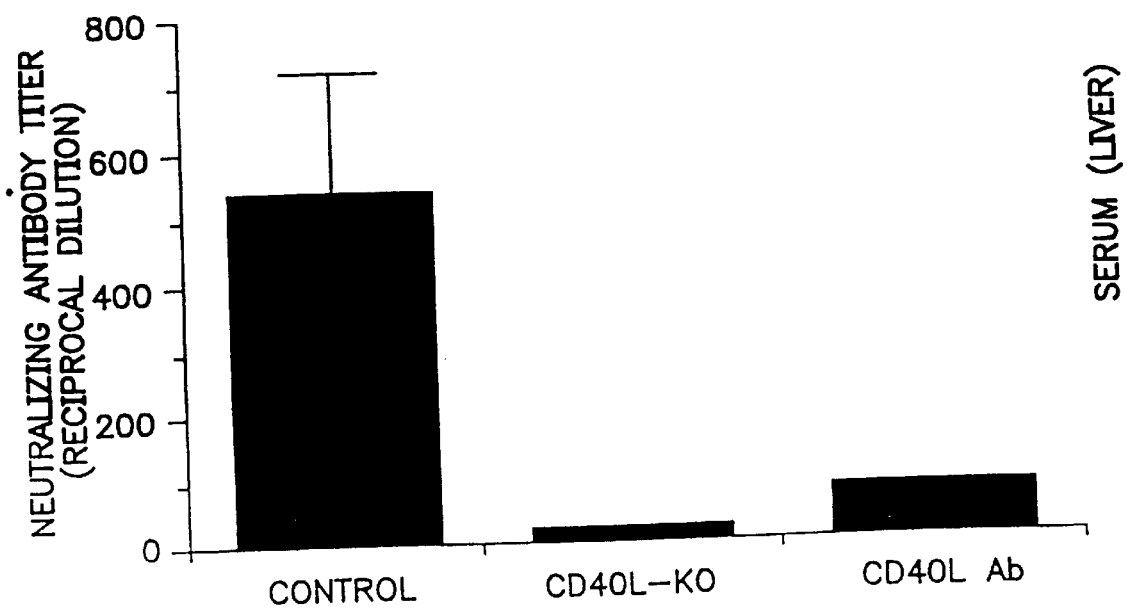
FIG. 6B is a bar chart as described in FIG. 6A, with data obtained from serum for the liver experiment of Example 7.
Figure 7A:
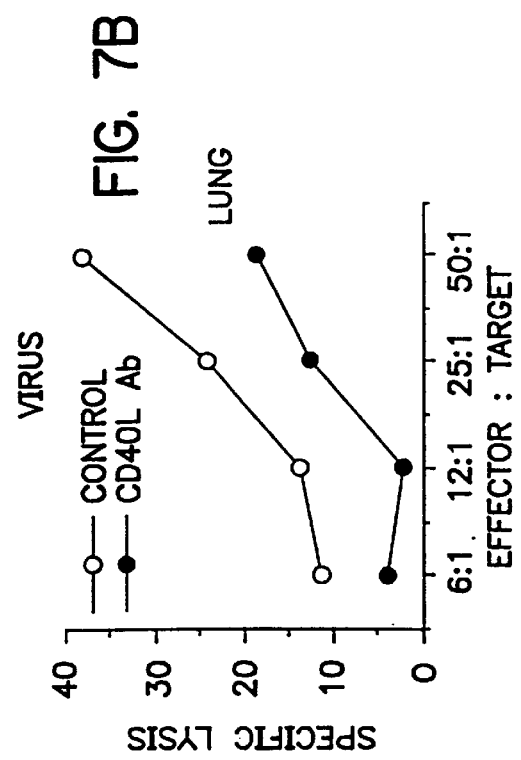
FIG. 7A is a line graph comparing the percentage of specific lysis in lymphocytes harvested from control C57BL/6 mice (open circles) and C57BL/6 mice treated with antibody to CD40L (filled circles). Seven days after virus administration, the lymphocytes were restimulated in vitro for 5 days and tested for specific lysis on mock-infected C57SV cells in a 6 hour $^{51}$Cr release assay. Percentage of specific lysis is expressed as a function of different effector to target ratios (6:1, 12:1, 25:1, and 50:1). Splenocytes were used for this lung experiment.
Figure 7B:
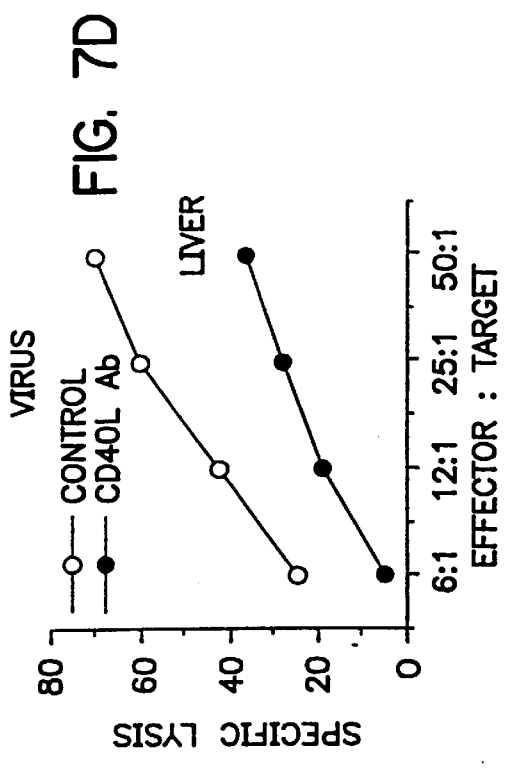
FIG. 7B is a line graph as described in FIG. 7A, using virus-infected C57SV cells.
Figure 7C:
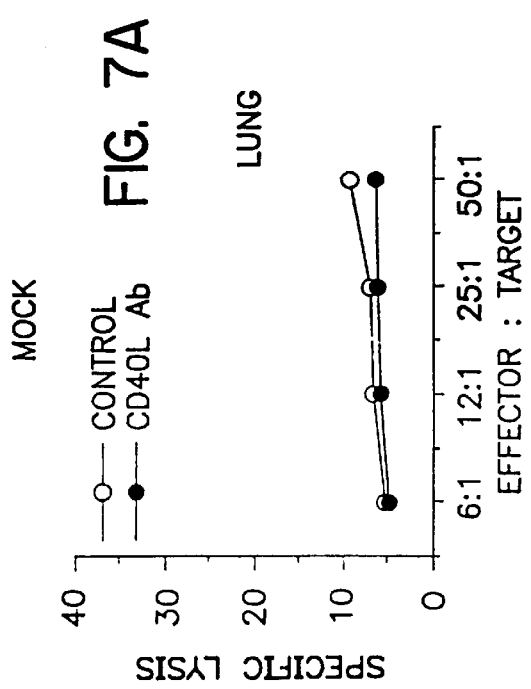
FIG. 7C is a line graph as described in FIG. 7A, using mock-infected cells. Mediastinal lymph node (MLN) cells were used for these liver experiments.
Figure 7D:
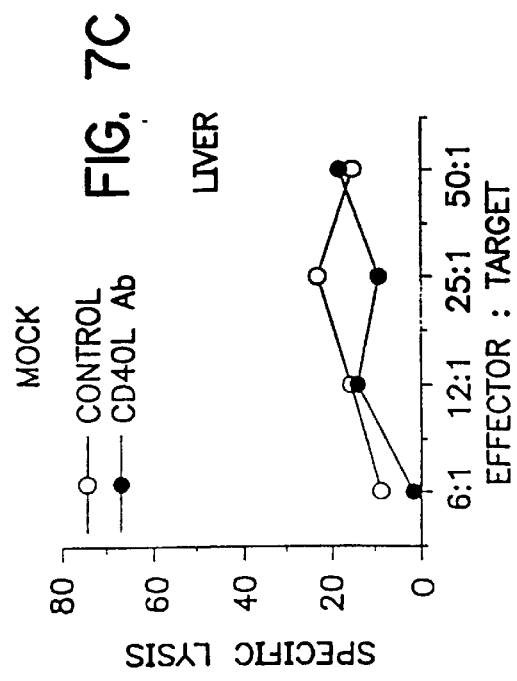
FIG. 7D is a line graph as described in FIG. 7A, using virus-infected cells. MLI cells were used for these liver experiments.

Normal litter mates that were administered vectors demonstrated high level transgene expression at day 3 in lung and liver that diminished to undetectable levels by day 28 (similar to what is seen in naive C57BL/6 mice; Table II). Serum and bronchial alveolar lavage (BAL) were analyzed for neutralizing antibody to human Ad5 as described in Y. Dai et al, *Proc. Natl. Acad. Sci. USA*, 92:1401–1405 (1995). Substantial neutralizing antibody developed to adenoviral capsid proteins by day 28 in either BAL fluid of animals that received vector intratracheally or in blood of animals that received vector into the venous circulation (FIG. 6). Readministration of vector on day 28 was unsuccessful as evidenced by the lack of transgene expression in the target organ 3 days later (similar to what is seen in C57BL/6 mice, Table II). Substantially different results were obtained in the CD40L deficient mice. Transgene expression was stable with little diminution for 28 days in both lung and liver (Table II). In addition, neutralizing antibody failed to develop (FIG. 6), resulting in highly efficient transgene expression following a second administration of virus (Table I).

EXAMPLE 8
Transient Blockade of CD40 Ligand with Antibody Prevents Primary T Cell Activation and Prolongs Transgene Exoression The following example demonstrates that transient inhibition of CD40L with antibody blocked CD4⁺ T cell priming in the lung model of gene therapy and effectively eliminated CD4 T and B cell effector responses. The persistent transgene expression and efficiency of vector readministration into the lung was essentially identical in animals genetically deficient in CD40L (Example 7 above) as compared to those transiently inhibited with CD40L antibody (see below).

The encouraging results obtained in the CD40L deficient mice as shown in Example 7 above provided a basis for developing an adjunct gene therapy with adenoviral vectors based on pharmacologic inhibition of CD40L signaling. This therapy is based upon findings that the capsid proteins of the input virus are the primary source of antigen for $CD4^+$ T cell activation, thereby restricting the time of costimulatory blockade to a short interval when vector is administered.

Experiments in C57BL/6 mice (six weeks of age, females) not treated with antibody or treated with isotype control antibody demonstrated high level transgene expression at day 3 in lung (Table II) and liver (Table II), that diminished to undetectable levels by day 28 (Table II). Gene transfer experiments were also performed in C57BL/6 animals injected with 100 µg mAb to CD40L (MR1, ATCC Hybridoma HB11048) i.p. on days −3, 0, +3 and +6 relative to the initial vector administration or equivalent quantities of a control hamster monoclonal antibody. Studies in murine lung demonstrated stabilization of transgene expression in CD40L mAb treated animals: the number of airways showing transgene in >25% of epithelial cells showed minimal decline from 72% on day 3 to 42% on day 28 (Table II). Transgene expression was also stabilized in liver of animals treated with CD40L mAb, in which transgene expressing hepatocytes diminished slightly from 89% to 47% over a 28 day interval (Table II). Transgene expression is stabilized in CD40L antibody treated animals at least 6 weeks, which is the longest time point evaluated (data not shown).

Recipient animals were analyzed for antigen specific activation of $CD4^+$ and $CDB^+$ T cells using both in vitro and in vivo assays. The effect of CD40L blockade on $CD4^+$ T cells was studied in proliferation assays of lymphocytes stimulated with UV-inactivated adenovirus essentially as described below (Table III). Briefly, lymphocytes of mediastinal lymph nodes (for lung experiment) or splenocytes (for liver experiment) from mice 10 days after administration of viruses were restimulated with UV-inactivated virus for 24 hours. Supernatants were tested on HT-2 cells (ATCC, CRL 1841) for cytokine secretion, and proliferation was assessed 72 hours later by measuring $^3H$-thymidine incorporation. Activation of adenoviral specific T cells, as quantified by the stimulation index, was documented initially at day 7 in nonantibody treated animals that were administered via vector into lung or liver. Activation of adenoviral specific T cells increased progressively over the ensuing 14 days. Stimulation index was calculated by dividing $^3H$ counts in the presence of antigen by those in the absence of antigen. T cell activation was substantially inhibited in both models by coadministration of CD40L antibody. The greatest inhibition was observed in animals administered vector into lung.

TABLE III $CD4^+$T Cell Responses and Neutralizing Antibody

|  | Stimulation Index[1] | Neutralizing Antibody[2] | |
| --- | --- | --- | --- |
|  | Day 7 | Day 21 | Day 28 |
| Lung |  |  |  |
| Control | 11.2 ± 1.1 | 52 ± 2 | 267 ± 92 |
| CD40L Ab | 1.2 ± 0.1 | 10 ± 1 | 20 ± 0 |
| CD40L KO | N.D. | N.D. | 20 ± 0 |
| Liver |  |  |  |
| Control | 20 ± 1 | 53 ± 2 | 533 ± 185 |
| CD40L Ab | 4.1 ± 0.5 | 21 ± 1 | 66 ± 23 |
| CD40L KO | N.D. | N.D. | 20 ± 0 |

[1]Data are presented as the mean stimulation index of three determinations ± 1 S.D. N.D. - Not determined.
[2]Data are presented as the mean neutralizing antibody titer (reciprocal dilution) of three samples ± S.D.

Activation of $CD8^+$ T cells by virus-infected cells was analyzed in chromium release assays using MHC H-2 compatible target cells infected with adenoviral vectors. As shown previously, specific lysis was demonstrated with lymphocytes harvested from C57BL/6 recipients on day 7, which were stimulated in vitro with adenovirus infected antigen presenting cells, and incubated with adenoviral infected targets (FIG. 7). No lysis was demonstrated to mock infected targets.

Lymphocytes harvested from animals treated with CD40L antibody also demonstrated CTL activity to adenovirus infected cells. However, the extent of lysis was consistently lower than that obtained from immune ablated animals. The necessity to amplify CTL by in vitro stimulation prior to the cytolytic assay may obscure more significant differences in CTL activation that occurred following the primary exposure in vivo.

The primary effect of CD40L inhibition on the activation of adenoviral specific $CD4^+$ T cells was further evaluated in vivo using techniques of immunocytochemistry. These experiments were restricted to the model of liver directed gene transfer because of technical limitations of immunofluorescence in lung sections. Liver tissues were analyzed on day 14 for infiltration of $CD4^+$ and $CD8^+$ T cells by double immunofluorescence. Nonantibody treated animals showed a typical mixed lymphocyte infiltrate that was dominated by $CD4^+$ T cells and associated with substantial upregulation of MHC class I on the basolateral surface of hepatocytes. Previous studies have suggested that secretion of IFN-γ from $T_{H1}$ activated $CD4^+$ T cells contributes to the increase in MHC class I which may sensitize the hepatocytes to CTL mediated elimination. Animals treated with antibody to CD40L still mobilized a mixed lymphocyte infiltrate. However, the proportion of $CD4^+$ T cells is substantially lower and the increase in MHC class I is substantially blunted. The specificity of the immunofluorescence assays was demonstrated in mock infected animals.

EXAMPLE 9

CD40L Antibody Prevents Formation of Blocking Antibody in Lung Directed Gene Transfer The impact of transient blockade of CD40L signaling at the time of vector administration on the production of neutralizing antibody and efficiency of repeated vector administration was evaluated in this experiment. Animals that received vector on day 0 with or without mAb were retreated with an adenoviral vector containing a different reporter gene on day 28. Blood was analyzed prior to administration of the second vector for neutralizing antibodies, and tissues were harvested for analysis of reporter gene expression 3 days later (i.e., day 31).

The most impressive results were obtained in the model of lung directed gene therapy. The development of neutralizing antibody in BAL following lung-directed gene transfer of vector was inhibited 20-fold in animals administered CD40L antibody (FIG. 7). Gene transfer with the second vector was unsuccessful in nonantibody treated animals or animals treated with an isotype control mAb (data not shown), as evidenced by the complete absence of transgene expression 3 days after vector readministration. This contrasts with animals treated during the first vector administration with CD40L antibody in which gene transfer was accomplished following a second administration of vector. Transgene expression was detected in >25% of airway epithelial cells of 30% of airways following the second vector, which is only slightly lower than the number of airways that express transgene in a naive animal treated with vector (i.e., 75%; Table II). Antibody to CD40L partially blocked the production of neutralizing antibody in serum following intravenous infusion of virus (FIG. 7). This was sufficient to enable some gene transfer to liver with the second vector (8% of hepatocytes), that did not occur in the absence of antibody, but is substantially reduced from that achieved following a primary administration of vector in a naive animals (89%)

EXAMPLE 10

Short Course of Cyclophosphamide Prevents Destructive Immune Responses in Mouse Luna and Liver C57BL/6 mice were given cyclophosphamide in various dosing regimens at the time an E1-deleted lacZ virus was administered into the blood, to study liver directed gene transfer, and into the trachea, to study lung directed gene transfer. A second E1-deleted virus, expressing the alkaline phosphatase reporter gene, is readministered into the same organ that received the first vector. Lymphocytes were isolated from regional sites and evaluated in vitro for vector specific T cell activation. Tissues were harvested at various times for analysis of inflammation and its consequences as well as expression of both the lacZ and ALP reporter genes.

A. Animal Studies

C57BL/6 female mice were injected with $1 \times 10^9$ pfu H5.010CMVlacZ via trachea (lung studies) or tail vein (liver studies) on day 0. Cyclophosphamide injections were given iv as indicated (in 200 ml PBS). H5.010CBALP was injected as described above on day 28. Animals were sacrificed on day 3, 28, 31 and 50 for analysis of transgene expression. When necropsy was performed, lung and liver tissues were prepared for cryosections, while spleen, bronchial alveolar lavage (BAL) and mediastinal lymph nodes (MhN) were harvested for immunological assays.

B. Morphological Analyses

For immunocytochemical analyses, frozen liver tissue was cryosectioned, while lungs were inflated with a 1:1 mixture of PBS/OTC, frozen and blocks cryosectioned. For X-Gal (5-bromo-4-chloro-3-indolyl b-D-galactopyranoside) histochemistry frozen 6 mm tissue sections were fixed in 0.5% glutaraldehyde for 10 min, washed twice with PBS containing 1 mM $MgCl_2$, and incubated in 1 mg of X-Gal per ml, 5 mM $K_3Fe(CN)_6$, 5 mM $K_4Fe(CN)6$, and 1 mM $MgCl_2$ in PBS for 4 hours. For alkaline phosphatase staining, frozen sections were fixed in 0.5% glutaraldehyde for 10 minutes and washed twice in PBS. The sections were incubated at 65° C. for 30 minutes to inactivate endogenous alkaline phosphatase activity, washed once in PBS and stained in 100 mM Tris-HCl (pH 9.5), 100 mM NaCl, 50 mM $MgCl_2$ containing 0.165 mg of BCIP (5-bromo-4-chloro-3-indolyl phosphate) and 0.33 mg of nitroblue tetrazolium per ml at 37° C. for 30 minutes.

C. Immunofluorescence

Frozen sections were fixed in −20° C. methanol for 10 minutes, air dried and rehydrated in PBS twice and unspecific binding blocked in 10% goat serum/PBS for 30 minutes. Sections were incubated for 1 hours with either rat-anti-mouse CD4 antibody (anti L3T4, GibcoBRL, 1:100 dilution in 2% goat serum), followed by a 30 minutes incubation with 5 mg of goat anti-rat immunoglobulin G (IgG)-fluorescein or rat-anti mouse CD8a-fluorescein isothiocyanate (anti-Ly-2, GibcoBRL, 1:100 dilution in 2% goat serum). For MHC class I staining, sections were incubated with 1:50 diluted mouse hybridoma supernatant to H-2K$^b$D$^b$ (20-8-4S) for 60 minutes, followed by a 30 minutes incubation with 5 mg/ml goat anti-mouse IgG-conjugated fluorescein isothiocyanate (FITC). Sections were washed twice and mounted with the antifadent Citifluor (Canterbury Chemical Lab., Canterbury, UK).

D. CTL Assay

For CTL assays, splenocytes from three mice or lymphocytes from 10 mice were pooled. Cells were restimulated in vitro for 5 days with H5.010CMVlacZ (MOI 0.5) and assayed on MHC-compatible target cells, which were previously infected with H5.010CMVlacZ and loaded with $^{51}Cr$, using different effector/target cell ratios. The percentage of specific $^{51}Cr$ release was calculated as [(cpm of sample−cpm of spontaneous release)/(cpm of maximum release−cpm of spontaneous release)]×100. Spontaneous release was determined by assaying target cells without effector cells in medium, while maximum release was estimated by adding 5% SDS to the target cells during the 6 hours incubation time.

E. Cytokine Release Assay $6 \times 10^6$ splenocytes were cultured with or without antigen (i.e., UV-inactivated H5.010CMVlacZ at a MOI of 10) for 24 h in a 24 well plate. 100 ml of cell-free supernatant were transferred onto $2 \times 10^3$ HT-2 cells (IL-2 and IL-4 dependent cell line) in round bottom 96 well plates. Medium and 10% rat concanavalin A supernatant were used as negative and positive controls. Proliferation was determined 48 h later by a 6 h [$^3$H]thymidine (0.35 mCi/well) pulse.

F. Neutralizing Antibody Assay

Serum and BAL were incubated for 30 min at 56° C. to inactivate complement. Serial dilutions of serum and BAL in DMEM without FBS (50 ml, starting at 1:20) were incubated with $1 \times 10^6$ pfu of H5.010CMVlacZ for 60 min and applied onto $2 \times 10^4$ Hela cells (80% confluent) in 96 well plates. After a 60 minutes incubation, 100 ml of DMEM containing 20% FBS were added. The cells were fixed 16–18 hours later and stained for β-galactosidase activity. All of the cells stained blue when medium was added instead of serum or BAL. The neutralizing antibody titer was determined by the highest dilution with which less than 50% of cells stained blue.

All articles identified herein are incorporated by reference. Numerous modifications and variations of the present invention are included in the above-identified specification and are expected to be obvious to one of skill in the art. Such modifications and alterations including the specific immune modulator selected, the manner of administration, the recombinant vector and transgene selected, route of administration, etc. are believed to be encompassed in the scope of the claims appended hereto.

What is claimed is:

1. In a method for repeated delivery of a recombinant virus to a mammal, said method comprising the step of administering to said mammal a recombinant virus comprising a transgene, wherein the improvement comprises the steps of co-administering with said recombinant virus an immune modulator which inhibits the formation of neutralizing antibodies against said virus, wherein said immune modulator is gamma-interferon; and re-administering the recombinant virus to said mammal, whereby the inhibition of formation of neutralizing antibodies to the recombinant virus by the immune modulator permits re-administration of the recombinant virus.

2. The method according to claim 1, wherein said recombinant virus is a recombinant adeno-associated virus.

3. In a method for repeated delivery of a recombinant virus to a mammal, said method comprising the step of administering to said mammal a recombinant virus comprising a transgene, wherein the improvement comprises the steps of co-administering with said recombinant virus an immune modulator which inhibits the formation of neutralizing antibodies against said virus, wherein said immune modulator is selected from the group consisting of a soluble CTLA4 and an anti-CTLA4 antibody; and re-administering the recombinant virus to said mammal, whereby the inhibition of formation of neutralizing antibodies to the recombinant virus by the immune modulator permits re-administration of the recombinant virus.

4. The method according to claim 3, wherein the recombinant virus is a recombinant adeno-associated virus.

5. In a method for repeated delivery of a recombinant virus to a mammal, said method comprising the step of administering to said mammal a recombinant virus comprising a transgene, wherein the improvement comprises the steps of co-administering with said recombinant virus an immune modulator which inhibits the formation of neutralizing antibodies against said virus wherein said immune modulator comprises a combination of cyclophosphamide and anti-CD4 monoclonal antibody; and re-administering the recombinant virus to said mammal, whereby the inhibition of formation of neutralizing antibodies to the recombinant virus by the immune modulator permits re-administration of the recombinant virus.

6. The method according to claim 5, wherein the recombinant virus is a recombinant adeno-associated virus.

7. In a method for repeated delivery of a recombinant virus to a mammal, said method comprising the step of administering to said mammal a recombinant virus comprising a transgene, wherein the improvement comprises the steps of co-administering with said recombinant virus an immune modulator which inhibits the formation of neutralizing antibodies against said virus wherein said immune modulator comprises interleukin-12; and re-administering the recombinant virus to said mammal, whereby the inhibition of formation of neutralizing antibodies to the recombinant virus by the immune modulator permits re-administration of the recombinant virus.

8. The method according to claim 7, wherein the recombinant virus is a recombinant adeno-associated virus.

* * * * *

UNITED STATES PATENT AND TRADEMARK OFFICE
CERTIFICATE OF CORRECTION

PATENT NO.    : 6,372,208 B1
DATED         : April 16, 2002
INVENTOR(S)   : James M. Wilson et al.

It is certified that error appears in the above-identified patent and that said Letters Patent is hereby corrected as shown below:

Column 3,
Line 34, replace "H5.010CKVLDLR" with -- H5.010CMVLDLR --.

Column 4,
Line 15, replace "MLI cells were used for these liver" with -- MLN cells were used for these liver --.

Column 8,
Line 47, replace "vectorsuseful" with -- vectors useful --.

Column 9,
Line 48, replace "totransfect" with -- to transfect --.

Column 10,
Line 18, replace "vector-used" with -- vector used --.

Column 13,
Line 57, replace "H5.010BALP." with -- H5.010CBALP. --.

Column 15,
Line 25, replace "expression-was" with -- expression was --.
Line 66, replace "etailed" with -- detailed --.

Column 16,
Line 25, replace "("β2⁻ mice");" with -- ("β2m⁻ mice"); --.

Column 17,
Line 18, replace "mals deficient in CDS cells and MHC class I.by virtue of a" with -- mals deficient in CD8 cells and MHC class I by virtue of a --.
Line 34, Example 5, replace "5.010CMVLDLR" with -- H5.010CMVLDLR --.

Column 18,
Line 19, replace "DMEK" with -- DMEM --.

UNITED STATES PATENT AND TRADEMARK OFFICE
CERTIFICATE OF CORRECTION

PATENT NO.    : 6,372,208 B1
DATED         : April 16, 2002
INVENTOR(S)   : James M. Wilson et al.

It is certified that error appears in the above-identified patent and that said Letters Patent is hereby corrected as shown below:

Column 19,
Line 31, replace "(c57SV," with -- (C57SV, --.

Column 20,
Line 19, Table II, replace "exprassion)" with -- expression --.
Lines 54 and 55, Example 8, replace "Exores-sion" with -- Expres-sion --.

Column 21,
Line 24, replace "CDB$^+$" with -- CD8$^+$ --.
Line 64, replace "± S.D." with -- ±1 S.D. --.

Column 23,
Line 6, Example 10, "Luna and liver" with -- Lung and liver --.
Line 27, replace "(MhN) were" with -- (MLN) were --.

Signed and Sealed this

Twenty-fourth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.    : 6,372,208 B1
DATED         : April 16, 2002
INVENTOR(S)   : James M. Wilson et al.

It is certified that error appears in the above-identified patent and that said Letters Patent is hereby corrected as shown below:

Column 13,
Table 1, line 30, replace "IFN-g" with -- IFN-γ --.
Table 1, line 32, replace "HIU mIL$^d$" with -- (IU/ml)$^d$ --.

Signed and Sealed this

Twentieth Day of July, 2004

JON W. DUDAS
*Acting Director of the United States Patent and Trademark Office*